United States Patent
Watanabe et al.

(10) Patent No.: US 12,312,371 B2
(45) Date of Patent: May 27, 2025

(54) OPTICALLY-ACTIVE 2-AMINO-PHOSPHONOALKANE ACID, OPTICALLY-ACTIVE 2-AMINO-PHOSPHONOALKANE ACID SALT, AND HYDRATES OF THESE

(71) Applicants: NAHLS CORPORATION CO., LTD., Kyoto (JP); KYOTO UNIVERSITY, Kyoto (JP)

(72) Inventors: Bunta Watanabe, Kyoto (JP); Ryuzo Yoshioka, Osaka (JP); Hideaki Ishida, Yamaguchi (JP)

(73) Assignees: NAHLS CORPORATION CO., LTD., Kyoto (JP); KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 17/530,612

(22) Filed: Nov. 19, 2021

(65) Prior Publication Data

US 2022/0135603 A1    May 5, 2022

Related U.S. Application Data

(62) Division of application No. 16/605,645, filed as application No. PCT/JP2018/015606 on Apr. 13, 2018, now Pat. No. 11,220,521.

(30) Foreign Application Priority Data

Apr. 17, 2017 (JP) .................... 2017-081237

(51) Int. Cl.
*C07F 9/38*         (2006.01)
*A61K 31/662*       (2006.01)

(52) U.S. Cl.
CPC .................. *C07F 9/3813* (2013.01)

(58) Field of Classification Search
CPC ........ C07F 9/3813; C07F 9/3808; A61K 8/55; A61K 31/662; A61P 17/00; A61P 17/04; A61Q 19/00
USPC ......................................................... 514/563
See application file for complete search history.

(56) References Cited

U.S. PATENT DOCUMENTS

| | | |
|---|---|---|
| 5,294,734 A | 3/1994 | Angst et al. |
| 5,767,309 A | 6/1998 | Knorr et al. |
| 5,869,668 A | 2/1999 | Knorr et al. |
| 2003/0003141 A1 | 1/2003 | Green et al. |
| 2005/0215513 A1 | 9/2005 | Boojamra et al. |
| 2008/0317834 A1 | 12/2008 | Green et al. |

FOREIGN PATENT DOCUMENTS

| | | |
|---|---|---|
| FR | 2511379 | 2/1983 |
| GB | 2 104 079 A | 3/1983 |
| JP | 58-131958 A | 8/1983 |
| JP | S60-112795 A | 6/1985 |
| JP | 3-130296 A | 6/1991 |

(Continued)

OTHER PUBLICATIONS

Registry STN Substance Record for 335150-85-1, May 10, 2001.*

(Continued)

*Primary Examiner* — Ana Z Muresan
(74) *Attorney, Agent, or Firm* — Sughrue Mion, PLLC

(57) ABSTRACT

A novel compound has pharmacological activities comparable to those of Nahlsgen and is storable excellently stably. The compound can be produced by a method according to the present invention for producing an optically active 2-amino-phosphonoalkanoic acid salt. In the method, a starting material DL-2-amino-phosphonoalkanoic acid represented by Formula (1) or a hydrate thereof is reacted with an optically active basic compound other than an optically active lysine, to give a diastereomeric salt mixture including a first salt (including a hydrate salt) between a D-2-amino-phosphonoalkanoic acid represented by Formula (1-1) and the optically active basic compound, and a second salt (including a hydrate salt) between an L-2-amino-phosphonoalkanoic acid represented by Formula (1-2) and the optically active basic compound. The diastereomeric salt mixture is fractionally crystallized to isolate one of the first and second diastereomeric salts.

[Chem. 1]

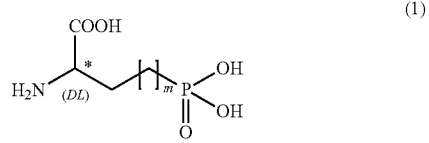

(1)

[Chem. 2]

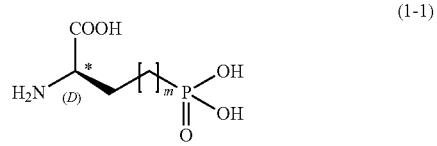

(1-1)

[Chem. 3]

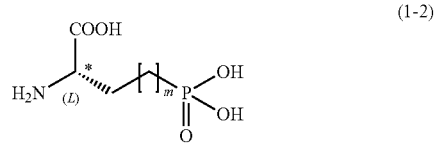

(1-2)

2 Claims, 9 Drawing Sheets

(56) References Cited

FOREIGN PATENT DOCUMENTS

| JP | 9-509924 A | 10/1997 |
| JP | 2003-532656 A | 11/2003 |
| JP | 2007-254479 A | 10/2007 |
| JP | 2010-270115 A | 12/2010 |

OTHER PUBLICATIONS

Chekhlov, Izvestiya Akademi Nauk, Seriya Khimicheskaya (1992), (11), 2561-5.*
March's Advanced Organic Chemistry (5th Ed. 2001), 151-155.*
Real World Drug Discovery, Rydzewski (2008), 42-43.*
CAS Registry No. 335150-85-1, Database Registry, May 10, 2001 (accession date), 1 page.
Christian Lherbet, et al., "Probing the sterochemistry of the active site of gamma-glutamyl transpeptidase using sulfur derivitives of L-glutamic acid", Organic & Biomolecular Chemistry, Dec. 2, 2003, pp. 238-245.
Extended European Search Report issued Dec. 15, 2020 by the European Patent Office in application No. 18788320.2.
International Search Report for PCT/JP2018/015606 dated Jul. 10, 2018 [PCT/ISA/210].
Schroer et al. AlChE Journal Feb. 2001 vol. 47, 368.
Notice of Reasons for Refusal issued Feb. 22, 2022 in Japanese Application No. 2019-513616.
Derek H.R. Barton et al., "The Invention of Radical Reactions. Part 39. The Reaction of White Phosphorus with Carbon-Centered Radicals. An Improved Procedure for the Synthesis of Phosphonic Acids and Further Mechanistic Insights", Tetrahedron, 1998, vol. 54, pp. 12475-12496 (22 pages total).
Peter M. Udvarhelyi et al, "Direct separation of amino acid enantiomers using a chiral crown ether stationary phase", Journal of Chromatography, 1990, vol. 519, pp. 69-74 (6 pages total).
Kazuhide Serizawa, "A polymorphism of medicines and crystallisation", 2002, pp. 273, 278, 305-317 (17 pages total).
Kazimierz Antczak, "Separation of Racemic Phosphonic Analogues of Glutamic Acid", Phosphorus and Sulfur, 1985, vol. 22, No. 2, pp. 247-251 (5 pages total).
Shadanhojin Nihon Kagakukai et al., "Optical Resolution by Diastereomer Method", 1995, Nippon Chemical Society, Fifth Edition, vol. 1, pp. II-320 to II-322 (7 pages total).
Nobuto Minowa, et al.,"Asymmetric Synthesis of (+)—Phosphinothricin and (+)-2-Amino-4-Phosphonobutyric Acid" Tetrahedron Letters, 1984, vol. 25, No. 11 pp. 1147-1150 (5 pages).
Tsutomu Yokomatsu, et al.,"Lipase-Catalyzed Enantioselective Acylation of Prochiral 2-(ω-Phosphono) alkyl-1,3-Propanediols: Application to the Enantioselective Synthesis of ω-Phosphono-α-Amino Acids", Tetrahedron: Asymmetry, 1996, vol. 7, No. 9, pp. 2743-2754.
Gloria Reyes-Rangel, et al., "Enantioselective Synthesis of (S)-2-amino-3-phosphonopropionic acid, (S)-AP-3, and (R)-2-amino-4-phosphonobutanoic acid, (R)-AP-4, via diastereoselective azidation of (4R,5R)-trans-N-[(diethoxyphosphoryl)propionyl]—and (4R,5R)-trans-N-[(diethozyphosphoryl)butanoyl]hexahydrobenzoxazolidin-2-one", Tetrahedron, 2006, vol. 62, pp. 8404-8409 (7 pages).
Oscar Garcia-Barradas, et al., "Enantioselective Synthesis of both enantiomers of 2-amino-6-phosphonohexanoic acid [(R)-and (S)-AP6], a potent and specific agonist of AMPA receptor subtype", Tetahedron: Asymmetry, 1997, vol. 8, No. 9, pp. 1511-1514 (5 pages).
Zhurnal Obshchei Khimii, 1996, vol. 66, No. 7, pp. 1096-1099 (8 pages).
Kyoritsu Kabushiki Kaisha, "Kagaku Dictionary", 1962, vol. 8, pp. 167-168 (5 pages).
Notice of Reasons for Refusal dated Nov. 21, 2023 in Japanese Application No. 2022-166702.
A.N. Chekhlov, "Crystalline and Molecular Structure of DL-2-amino-4-phosphonobutyric acid monohydrate," Institute of Physiologically Active Compounds, Russian Academy of Sciences, 142432 Chernogolovka. Translated from Izvestiya Akademii Nauk, Seriya Khimicheskaya, No. 11, pp. 2561-2565, Nov. 1992. Original article submitted Nov. 21, 1991.

* cited by examiner

OPTICALLY-ACTIVE 2-AMINO-PHOSPHONOALKANE ACID, OPTICALLY-ACTIVE 2-AMINO-PHOSPHONOALKANE ACID SALT, AND HYDRATES OF THESE

CROSS-REFERENCE

This is a divisional of application Ser. No. 16/605,645, filed Oct. 16, 2019, which is a National Stage of International Application No. PCT/JP2018/015606, filed on Apr. 13, 2018, which claims priority to Japanese Patent Application No. 2017-081237, filed Apr. 17, 2017, the entire contents of which are incorporated herein by reference.

TECHNICAL FIELD

The present invention relates to optically active 2-amino-phosphonoalkanoic acids, optically active 2-amino-phosphonoalkanoic acid salts, and hydrates of them, as well as methods for producing these compounds.

BACKGROUND ART

Nahlsgen (registered trademark) or GGsTop (generic name: DL-2-amino-4-[(RSp)-(3-carboxymethylphenoxy)(methoxy)phosphoryl]butanoic acid) is known as an excellent gamma-glutamyl transpeptidase (GGT) inhibitor (for example, Patent Literature (PTL) 1).

Unfortunately, Nahlsgen is not crystallized, but is in an oily state at room temperature; and an amorphous powdery solid, which is finally obtained through lyophilization, is deliquescent and is liable to decompose at room temperature. This causes Nahlsgen to be stored as refrigerated or frozen and to be very difficult to handle.

CITATION LIST

Patent Literature

PTL 1: Japanese Unexamined Patent Application Publication (JP-A) No. 2010-270115

SUMMARY OF INVENTION

Technical Problem

Accordingly, the present invention has an object to provide a novel compound that has pharmacological activities comparable to those of Nahlsgen and offers superior storage stability, and to provide a method for producing the compound.

The present invention has another object to provide a method for efficiently isolating two optical isomers, which constitute a DL-2-amino-phosphonoalkanoic acid, from each other.

Solution to Problem

The inventors of the present invention have made intensive investigations to achieve the objects.

2-Amino-5-phosphonopentanoic acid and 2-amino-7-phosphonoheptanoic acid, which have a skeleton common to Nahlsgen, are each a mixture (racemate) of two optical isomers and are known to be optically resolved using an optically active lysine.

The inventors have found an optically active basic compound other than lysine, which compound can form salts having good crystallinity with a DL-2-amino-phosphonoalkanoic acid containing 4 to 10 total carbon atoms, such as 2-amino-5-phosphonopentanoic acid or 2-amino-7-phosphonoheptanoic acid.

The inventors have also found that a salt between a D- or L-2-amino-phosphonoalkanoic acid containing 4 to 10 total carbon atoms and the optically active basic compound, when isolated and subjected to a decomposition treatment, can easily and efficiently give the D- or L-2-amino-phosphonoalkanoic acid containing 4 to 10 total carbon atoms.

The inventors have also found that, among such salts, a salt between a D- or L-2-amino-phosphonoalkanoic acid containing 4, 6, or 8 total carbon atoms and the optically active basic compound, or a hydrate of the salt (namely, a hydrate salt) has especially excellent crystallinity; and that the salt or hydrate, when isolated and subjected to a decomposition treatment, can give a D- or L-2-amino-phosphonoalkanoic acid containing 4, 6, or 8 total carbon atoms, or a hydrate of the salt, efficiently with high purity.

In addition and advantageously, the inventors have found that such D- or L-2-amino-phosphonoalkanoic acids containing 4, 6, or 8 total carbon atoms obtained by the method, salts between them and the optically active basic compounds, and hydrates of them have pharmacological activities (such as a collagen production promoting activity, glutathione production promoting activity, and wound healing promoting activity) comparable to those of Nahlsgen, and offer superior storage stability. The present invention has been made on the basis of these findings.

Specifically, an aspect of the present invention provides a method for producing an optically active 2-amino-phosphonoalkanoic acid salt. The method includes reacting, as a starting material, a DL-2-amino-phosphonoalkanoic acid represented by Formula (1) or a hydrate thereof with an optically active basic compound other than an optically active lysine, to give a diastereomeric salt mixture containing a first salt (including a hydrate salt) between a D-2-amino-phosphonoalkanoic acid represented by Formula (1-1) and the optically active basic compound and a second salt (including a hydrate salt) between an L-2-amino-phosphonoalkanoic acid represented by Formula (1-2) and the optically active basic compound, and subjecting the diastereomeric salt mixture to fractional crystallization to isolate one of the first and second diastereomeric salts, where Formulae (1), (1-1), and (1-2) are expressed as follows:

[Chem. 1]

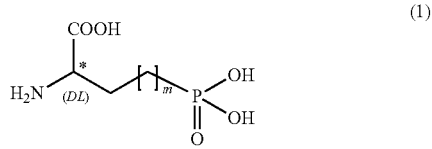

wherein m represents an integer of 1 to 7; and the asterisk (*) marks an asymmetric atom,

[Chem. 2]

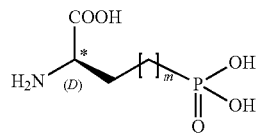

(1-1)

wherein m and the asterisk are as defined above,

[Chem. 3]

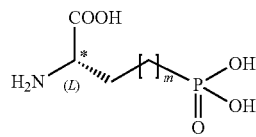

(1-2)

wherein m and the asterisk are as defined above.

In the method for producing an optically active 2-amino-phosphonoalkanoic acid salt, the optically active basic compound may be a compound selected from the group consisting of cinchonine, cinchonidine, quinine, quinidine, an optically active arginine, an optically active phenylalaninamide, an optically active ornithine, an optically active tyrosine hydrazide, an optically active 1-phenylpropylamine, an optically active 2-phenylpropylamine, an optically active valinol, an optically active p-hydroxyphenylglycine hydrazide, an optically active p-hydroxyphenylglycine methyl ester, an optically active p-hydroxyphenylglycine ethyl ester, an optically active glucamine, an optically active leucinol, an optically active 1-phenylethylamine, and an optically active 2-amino-1-butanol.

In the method, the starting material may be the DL-2-amino-phosphonoalkanoic acid represented by Formula (1) in which m is 1, 3, or 5, or a hydrate thereof.

In the method, the hydrate of the DL-2-amino-phosphonoalkanoic acid represented by Formula (1) is used as the starting material, to give, as one of the diastereomeric salts, the first salt between the D-2-amino-phosphonoalkanoic acid represented by Formula (1-1) and the optically active basic compound, or a hydrate of the first salt, or the second salt between the L-2-amino-phosphonoalkanoic acid represented by Formula (1-2) and the optically active basic compound, or a hydrate of the second salt.

Another aspect of the present invention provides a D-2-amino-phosphonoalkanoic acid salt or a hydrate of the salt, represented by Formula (1-1'-B):

[Chem. 4]

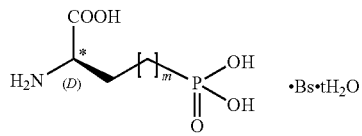

(1-1'-B)

wherein m' represents 1, 3, or 5; t represents a number of 0 to 5; Bs represents an optically active basic compound other than an optically active lysine; and the asterisk marks an asymmetric atom.

Still another aspect of the present invention provides an L-2-amino-phosphonoalkanoic acid salt or a hydrate of the salt, represented by Formula (1-2'-B):

[Chem. 5]

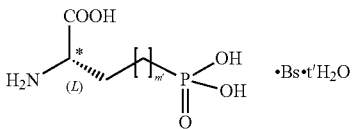

(1-2'-B)

wherein m' represents 1, 3, or 5; t' represents a number of 0 to 5; Bs represents an optically active basic compound other than an optically active lysine; and the asterisk marks an asymmetric atom.

Still another aspect of the present invention provides a method for producing an optically active 2-amino-phosphonoalkanoic acid or a hydrate thereof. The method includes preparing an optically active 2-amino-phosphonoalkanoic acid salt (including a hydrate salt) by the method for producing an optically active 2-amino-phosphonoalkanoic acid salt, and decomposing the prepared compound to give a corresponding optically active 2-amino-phosphonoalkanoic acid, or a hydrate thereof, having the same configuration as the compound before decomposition.

Still another aspect of the present invention provides a D-2-amino-phosphonoalkanoic acid hydrate represented by Formula (1-1'):

[Chem. 6]

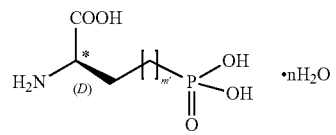

(1-1')

wherein m' represents 1, 3, or 5; n represents a number from greater than 0 to 5; and the asterisk marks an asymmetric atom.

Still another aspect of the present invention provides an L-2-amino-phosphonoalkanoic acid hydrate represented by Formula (1-2'):

[Chem. 7]

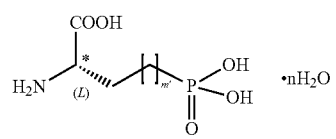

(1-2')

wherein m' represents 1, 3, or 5; n represents a number from greater than 0 to 5; and the asterisk marks an asymmetric atom.

Advantageous Effects of Invention

The DL-2-amino-phosphonoalkanoic acid represented by Formula (1), or a hydrate thereof, has a skeleton common to Nahlsgen, but can be produced easily and inexpensively as compared with Nahlsgen. From the compound, which is a mixture (racemate) of two optical isomers (diastereomeric salts), the method according to the present invention for producing an optically active 2-amino-phosphonoalkanoic acid salt can efficiently isolate one of the two diastereomeric salts (namely, one of a first salt (including a hydrate salt) between the D-2-amino-phosphonoalkanoic acid and the above-mentioned optically active basic compound, and a second salt (including a hydrate salt) between the L-2-amino-phosphonoalkanoic acid and the optically active basic compound). From the isolated diastereomeric salt, the method according to the present invention for producing an optically active 2-amino-phosphonoalkanoic acid or a hydrate thereof can easily give, as a decomposed product resulting from a decomposition treatment, an optically active D-2-amino-phosphonoalkanoic acid or a hydrate thereof, or an optically active L-2-amino-phosphonoalkanoic acid or a hydrate thereof with high purity.

Such diastereomeric salts and decomposed products of the salts obtained by the methods have excellent crystallinity. These compounds absorb approximately no moisture at room temperature and are non-deliquescent. Thus, the compounds are storable excellently stably and are easy to handle. The compounds have pharmacological activities (such as a collagen production promoting activity, glutathione production promoting activity, and promoting activity on wound healing typically in mucosa such as oral mucosa and ocular mucosa) comparable to those of Nahlsgen, have approximately no cytotoxicity, and are highly safe. Accordingly, the compounds are advantageously usable for the purpose of treatment and/or prophylaxis typically against skin diseases such as allergic skin diseases, ichthyosis vulgaris, and senile xerosis; and oral or ocular mucosal diseases such as periodontal diseases and conjunctivitis.

DESCRIPTION OF EMBODIMENTS

Figure 1:
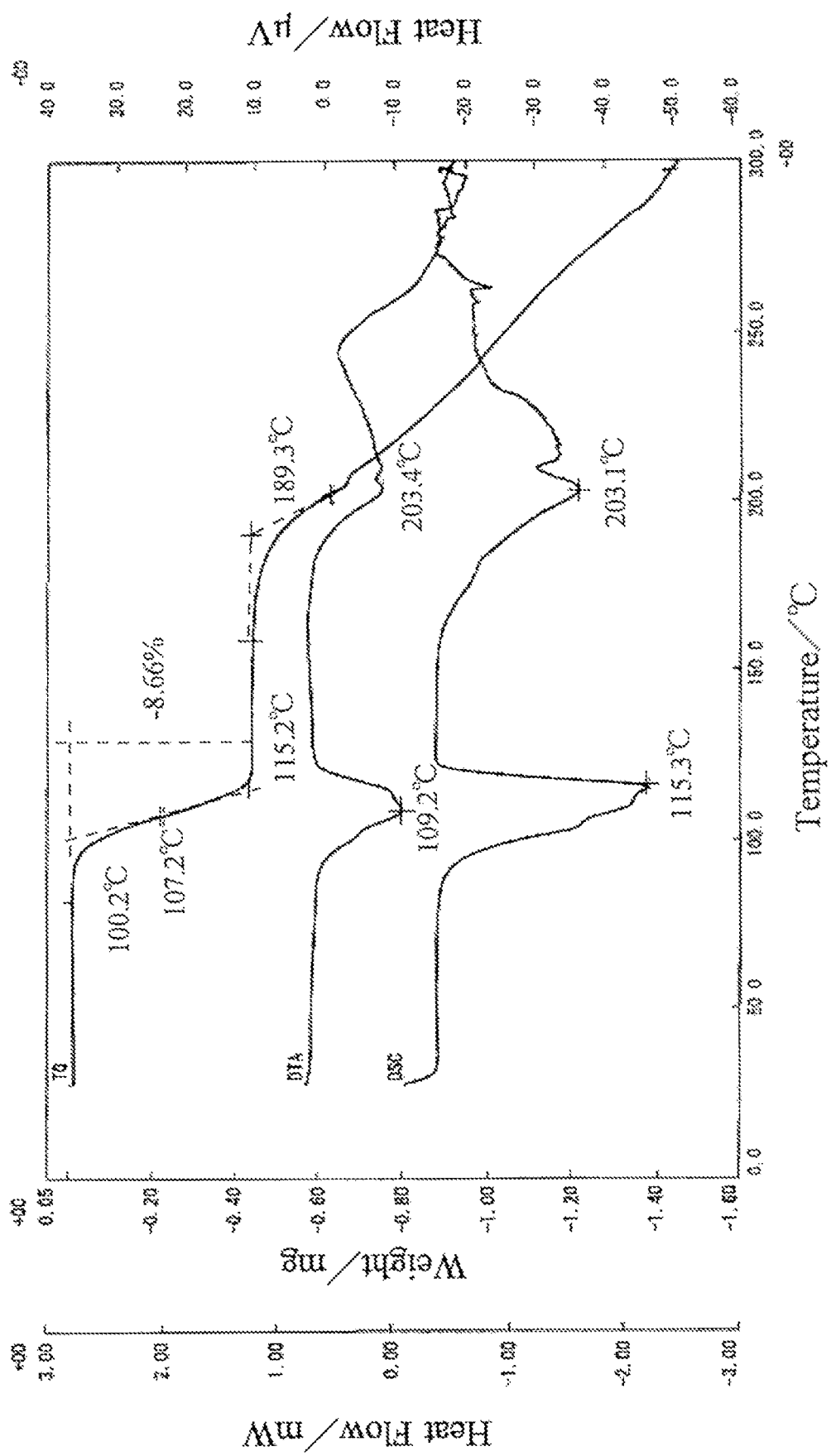
FIG. 1 is a chart illustrating thermal analysis results of DL-2-amino-4-phosphonobutanoic acid monohydrate prepared in Preparation Example 1.

Method for Producing Optically Active 2-Amino-Phosphonoalkanoic Acid Salt

A method according to an embodiment of the present invention for producing an optically active 2-amino-phosphonoalkanoic acid salt includes reacting and isolating. In the reacting, a starting material DL-2-amino-phosphonoalkanoic acid represented by Formula (1) (hereinafter also referred to as "DL-AP") or a hydrate thereof is reacted with an optically active basic compound other than an optically active lysine (hereinafter also referred to as "Bs"), to give a diastereomeric salt mixture (a mixture of a pair of salts in a diastereomeric relation). The mixture includes a first salt (including a hydrate salt) and a second salt (including a hydrate salt). The first salt is a salt between a D-2-amino-phosphonoalkanoic acid represented by Formula (1-1) (hereinafter also referred to as "D-AP") and the optically active basic compound. The second salt is a salt between an L-2-amino-phosphonoalkanoic acid represented by Formula (1-2) (hereinafter also referred to as "L-AP") and the optically active basic compound. In the isolating, the diastereomeric salt mixture is subjected to fractional crystallization to isolate one of the first and second diastereomeric salts (one of the pair of salts in a diastereomeric relation). In the following formulae, m represents an integer of 1 to 7; and the asterisk (*) marks an asymmetric atom. Formulae (1), (1-1), and (1-2) are expressed as follows:

[Chem. 8]

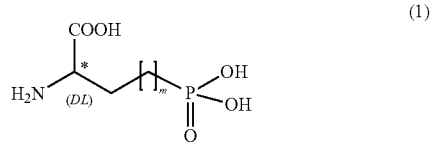

(1)

[Chem. 9]

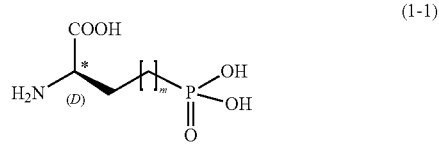

(1-1)

[Chem. 10]

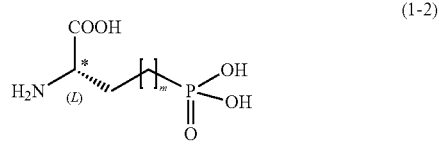

(1-2)

DL-AP has one asymmetric atom (*) in a molecule and is a mixture of two different optical isomers. In the formulae, (D) and (L) indicate the configurations of ligands bonded to the asymmetric atom, where the configurations are indicated in D/L notation. (D) indicates that the amino group appears to the right, and (L) indicates that the amino group appears to the left, in a Fischer projection in which the carboxy is laid upward. In the description, the configurations of optical isomers other than amino acids are indicated in R/S notation.

The starting material for use herein is preferably selected from, among others, compounds represented by Formula (1) in which m is 1, 3, or 5 (namely, DL-2-amino-phosphonoalkanoic acids containing 4, 6, or 8 total carbon atoms) or hydrates of the compounds, to give a diastereomeric salt having still better crystallinity.

The starting material for use herein is also preferably selected from hydrates of DL-AP, to give a diastereomeric salt having still better crystallinity.

Accordingly, the starting material is preferably selected from hydrates of the compounds represented by Formula (1) in which m is 1, 3, or 5 (namely, DL-2-amino-phosphonoalkanoic acid hydrates containing 4, 6, or 8 total carbon atoms).

Non-limiting examples of the optically active basic compound (Bs) include cinchonine, cinchonidine, quinine, quinidine, an optically active arginine, an optically active phenylalaninamide, an optically active ornithine, an optically active tyrosine hydrazide, an optically active 1-phenylpropylamine, an optically active 2-phenylpropylamine, an optically active valinol, an optically active p-hydroxyphenylglycine hydrazide, an optically active p-hydroxyphenylglycine methyl ester, an optically active p-hydroxyphenylglycine ethyl ester, an optically active glucamine, an optically active leucinol, an optically active 1-phenylethylamine, and an optically active 2-amino-1-butanol. Cinchonine and cinchonidine are mutually optical isomers; and quinine and quinidine are also mutually optical isomers. The optically active compound, when being an amino acid, includes D-form (D-Bs) and L-form (L-Bs). For example, the optically active arginine includes D-arginine and L-arginine. The optically active compound, when being a compound other than amino acids, includes R-form (R-Bs) and S-form (S-Bs). For example, the optically active 1-phenylpropylamine includes (R)-1-phenylpropylamine and (S)-1-phenylpropylamine.

DL-AP or a hydrate thereof reacts with the optically active basic compound to give a mixture (diastereomeric salt mixture) of a first salt between D-AP and the optically active basic compound, or a hydrate of the first salt; and a second salt between L-AP and the optically active basic compound, or a hydrate of the second salt.

For example, assume that an amino acid is used as the optically active basic compound (Bs). DL-AP or a hydrate thereof, when reacting with the L-form of the amino acid (L-Bs), gives a diastereomeric salt mixture including a pair of diastereomeric salts, i.e., a first salt between D-AP and the L-form (L-Bs), or a hydrate of the first salt; and a second salt between L-AP and the L-form (L-Bs), or a hydrate of the second salt. Similarly, DL-AP or a hydrate thereof, when reacting with the D-form of the amino acid (D-Bs), gives a diastereomeric salt mixture including a pair of diastereomeric salts, i.e., a first salt between D-AP and the D-form (D-Bs), or a hydrate of the first salt; and a second salt between L-AP and the D-form (D-Bs), or a hydrate of the second salt. This can be applied correspondingly to other cases employing optically active basic compounds other than amino acids.

The optically active basic compound is preferably selected and used appropriately according to the length of the alkane chain in DL-AP (namely, the value of m in Formula (1)). This is preferred for enabling the formation of a diastereomeric salt mixture including a diastereomeric salt having excellent crystallinity; and for enabling more efficient isolation of a diastereomeric salt with higher purity from the diastereomeric salt mixture by precipitating the one diastereomeric salt having excellent crystallinity from the mixture.

Preferred combinations of DL-AP or a hydrate thereof and the optically active basic compound are as follows.

In Formula (1):

when m is 1, namely, when DL-AP or a hydrate thereof is DL-2-amino-4-phosphonobutanoic acid or a hydrate thereof, the optically active basic compound is preferably selected from cinchonine, cinchonidine, quinine, quinidine, an optically active arginine (D- or L-arginine), an optically active phenylalaninamide (D- or L-phenylalaninamide), and an optically active ornithine (D- or L-ornithine);

when m is 3, namely, when DL-AP or a hydrate thereof is DL-2-amino-6-phosphonohexanoic acid or a hydrate thereof, the optically active basic compound is preferably selected from an optically active tyrosine hydrazide (D- or L-tyrosine hydrazide), an optically active 1-phenylpropylamine (R- or S-1-phenylpropylamine), an optically active valinol (D- or L-valinol), an optically active p-hydroxyphenylglycine methyl ester (D- or L-p-hydroxyphenylglycine methyl ester), an optically active phenylalaninamide (D- or L-phenylalaninamide), an optically active p-hydroxyphenylglycine hydrazide (D- or L-p-hydroxyphenylglycine hydrazide), and an optically active p-hydroxyphenylglycine ethyl ester (D- or L-p-hydroxyphenylglycine ethyl ester); and when m is 5, namely, when DL-AP or a hydrate thereof is DL-2-amino-8-phosphonooctanoic acid or a hydrate thereof, the optically active basic compound is preferably selected from an optically active glucamine (D- or L-glucamine), an optically active valinol (D- or L-valinol), an optically active leucinol (D- or L-leucinol), an optically active 1-phenylethylamine (R- or S-1-phenylethylamine), an optically active p-hydroxyphenylglycine hydrazide (D- or L-p-hydroxyphenylglycine hydrazide), and an optically active 2-amino-1-butanol (R- or S-2-amino-1-butanol).

The optically active basic compound is used in an amount of typically about 0.5 to about 2.0 moles, preferably 0.5 to 1.5 moles, and particularly preferably 0.6 to 1.1 moles, per mole of DL-AP or a hydrate thereof.

The reaction between DL-AP or a hydrate thereof and the optically active basic compound is preferably performed in the presence of a solvent. Non-limiting examples of the solvent include ketones such as acetone and methyl ethyl ketone; alcohols such as methanol, ethanol, and isopropyl alcohol; esters such as ethyl acetate; nitrogen-containing compounds such as acetonitrile; ethers such as tetrahydrofuran; and water. Each of different solvents may be used alone or in combination.

The solvent is used in an amount of typically about 1 to about 100 weight percent relative to the totality of DL-AP or a hydrate thereof and the optically active basic compound. The reaction, if performed in the presence of the solvent in an amount greater than the range, tends to proceed at a lower reaction rate, because of lower concentrations of the reaction components.

The reaction may be performed in any atmosphere harmless to the reaction, such as an air atmosphere, nitrogen atmosphere, or argon atmosphere.

The reaction is performed at a temperature of typically about 0° C. to about 100° C. for a time of typically about 1 to about 10 hours. The reaction may be performed according to any system such as a batch system, semi-batch system, or continuous system.

The method according to the present invention for producing an optically active 2-amino-phosphonoalkanoic acid salt (in particular, a process for fractionally crystallizing a diastereomeric salt mixture) will be illustrated below, while taking, as an example, the case where an amino acid (D-Bs or L-Bs) is used as the optically active basic compound (Bs). The following can be applied correspondingly to other cases employing optically active basic compounds other than amino acids.

In the diastereomeric salt mixture, a salt between D-AP and the L-form (L-Bs) or a hydrate of the salt differs in solubility in a solvent from a salt between L-AP and the L-form (L-Bs) or a hydrate of the salt. Likewise, a salt between D-AP and the D-form (D-Bs) or a hydrate of the salt differs in solubility in a solvent from a salt between L-AP and D-form (D-Bs) or a hydrate of the salt. The difference in solubility enables one of such diastereomeric salts to be easily isolated by fractional crystallization.

The salt between D-AP and the L-form (L-Bs) or a hydrate of the salt tends to have high crystallinity as compared with the salt between L-AP and the L-form (L-Bs) or a hydrate of the salt; and the salt between L-AP and the D-form (D-Bs) or a hydrate of the salt tends to have high crystallinity as compared with the salt between D-AP the D-form (D-Bs) or a hydrate of the salt. For example, each of the salt, or a hydrate thereof, between D-AP and the optically active basic compound; and the salt, or a hydrate thereof, between L-AP and the optically active basic compound can be isolated typically in the following manner. A DL-AP hydrate reacts with the L-form (L-Bs) to give a mixture (diastereomeric salt mixture) including the salt, or a hydrate thereof, between D-AP and the L-form (L-Bs) and the salt, or a hydrate thereof, between L-AP and the L-form (L-Bs). From the diastereomeric salt mixture, the salt, or a hydrate thereof, between D-AP and the L-form (L-Bs) initially precipitates out as crystals, and the crystals are collected and isolated by a filtration treatment. The filtration mother liquor is subjected to a decomposition treatment to convert the salt, or a hydrate thereof, between L-AP and the L-form (L-Bs) in the filtration mother liquor into an L-AP hydrate. The L-AP hydrate subsequently reacts with the D-form (D-Bs) to give the salt, or a hydrate thereof, between L-AP and the D-form (D-Bs), and the resulting salt or a hydrate thereof precipitates as crystals.

The crystals may precipitate out by any technique appropriately selected from well-known, common techniques such as cooling crystallization, poor solvent crystallization, evaporative crystallization, and pressure crystallization.

An embodiment of the method according to the present invention for producing an optically active 2-amino-phosphonoalkanoic acid salt will be illustrated below. A DL-AP hydrate to be used as the starting material is indicated as a "DL-AP·nH$_2$O", where n represents a number from greater than 0 to 5. Signs (t-1), (t-2), and (t-3) each represent, identically or differently, a number from 0 to 5.

[Chem. 11]

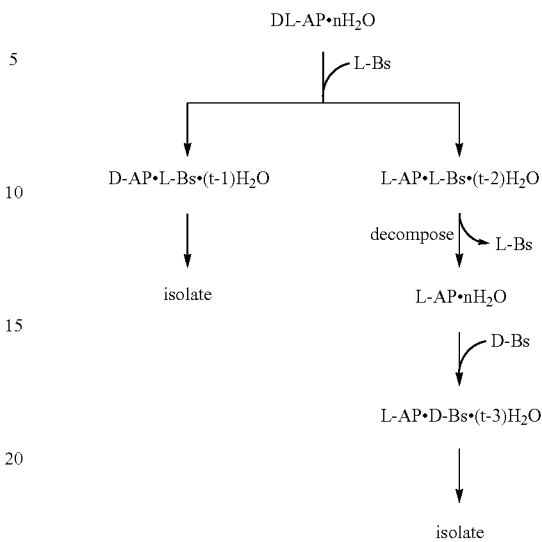

The present invention can isolate, as diastereomeric salts, a D-2-amino-phosphonoalkanoic acid or a hydrate thereof represented by Formula (1-1'-B) and a L-2-amino-phosphonoalkanoic acid salt or a hydrate thereof represented by Formula (1-2'-B) efficiently with high purity, where Formulae (1-1'-B) and (1-2'-B) are expressed as follows:

[Chem. 12]

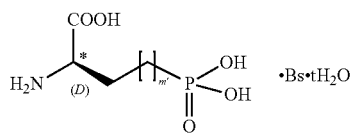

(1-1'-B)

wherein m' represents 1, 3, or 7; t represents a number of 0 to 5; Bs represents an optically active basic compound other than an optically active lysine; and the asterisk marks an asymmetric atom,

[Chem. 13]

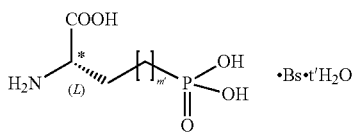

(1-2'-B)

wherein m' represents 1, 3, or 7; t' represents a number of 0 to 5; Bs represents an optically active basic compound other than an optically active lysine; and the asterisk marks an asymmetric atom.

In the D-2-amino-phosphonoalkanoic acid salt hydrate represented by Formula (1-1'-B):

when m' is 1, the optically active basic compound is preferably a compound selected from quinidine, cinchonidine, L-arginine, D-p-hydroxyphenylglycine hydrazide, and D-phenylalaninamide;

when m' is 3, the optically active basic compound is preferably L-tyrosine hydrazide; and when m' is 7, the optically active basic compound is preferably a compound selected from L-leucinol and (R)-2-amino-1-butanol.

In the L-2-amino-phosphonoalkanoic acid salt hydrate represented by Formula (1-2'-B):

when m' is 1, the optically active basic compound is preferably a compound selected from cinchonine and L-ornithine;

when m' is 3, the optically active basic compound is preferably a compound selected from (R)-1-phenylpropylamine, L-valinol, D-p-hydroxyphenylglycine methyl ester, D-phenylalaninamide, D-p-hydroxyphenylglycine hydrazide, and D-p-hydroxyphenylglycine ethyl ester; and when m' is 7, the optically active basic compound is preferably a compound selected from D-glucamine, L-valinol, (R)-1-phenylethylamine, and D-p-hydroxyphenylglycine hydrazide.

Optically active 2-amino-phosphonoalkanoic acid salts (including hydrates) (in particular, the D-2-amino-phosphonoalkanoic acid or a hydrate thereof represented by Formula (1-1'-B), and the L-2-amino-phosphonoalkanoic acid salt or a hydrate thereof represented by Formula (1-2'-B)) obtained by the methods absorb approximately no moisture at room temperature, are storable excellently stably, and are easy to handle. These compounds have approximately no cytotoxicity and are highly safe. In addition, the compounds have pharmacological activities (such as a collagen production promoting activity, glutathione production promoting activity, and wound healing promoting activity) comparable to those of Nahlsgen, enhance barrier functions of the skin, can prevent or reduce the entry of allergens, and can reduce allergic reactions. The compounds are advantageously usable for the treatment and/or prophylaxis of skin diseases such as allergic skin diseases, ichthyosis vulgaris, and senile xerosis. The compounds are also advantageously usable as healing promoters for mucosa such as oral mucosa and ocular mucosa, for the treatment and/or prophylaxis of oral mucosal diseases such as periodontal diseases, and ocular mucosal diseases such as conjunctivitis.

DL-AP or a hydrate thereof as the starting material can be produced typically by methods described in Non-Patent Literature (Kosolapoff G. M. Isomerization of Alkyl Phosphites. VII. Some Derivatives of 2-Bromoethanephosphonic Acid J. Am. Chem. Soc. 1948, 70, 1971-1972; Chambers, J. R., Isbell, A. F. A New Synthesis of Amino Phosphonic Acids. J. Org. Chem. 1964, 29, 832-836).

More specifically, DL-AP or a hydrate thereof can be produced through the reactions represented by the formulae below. In the formulae, m represents an integer of 1 to 7; n represents a number from greater than 0 to 5; X represents a halogen (such as fluorine, chlorine, bromine, or iodine); R and R' each represent, identically or differently, $C_1$-$C_{10}$ alkyl; R" represents an amino-protecting group; DPR represents a deprotectant for the amino group protected by the protecting group; and the asterisk marks an asymmetric atom. Non-limiting examples of the amino-protecting group include $C_1$-$C_{10}$ alkyls, $C_7$-$C_{18}$ aralkyls, acyls ($R^1C(=O)$ groups, where $R^1$ represents $C_1$-$C_{10}$ alkyl), alkoxycarbonyls ($R^2OC(=O)$ groups, where $R^2$ represents $C_1$-$C_{10}$ alkyl), optionally substituted benzyloxycarbonyl, optionally substituted phenylmethylidene, and optionally substituted diphenylmethylidene. Non-limiting examples of the substituents mentioned above include halogens, $C_1$-$C_3$ alkoxys, and nitro.

[Chem. 14]

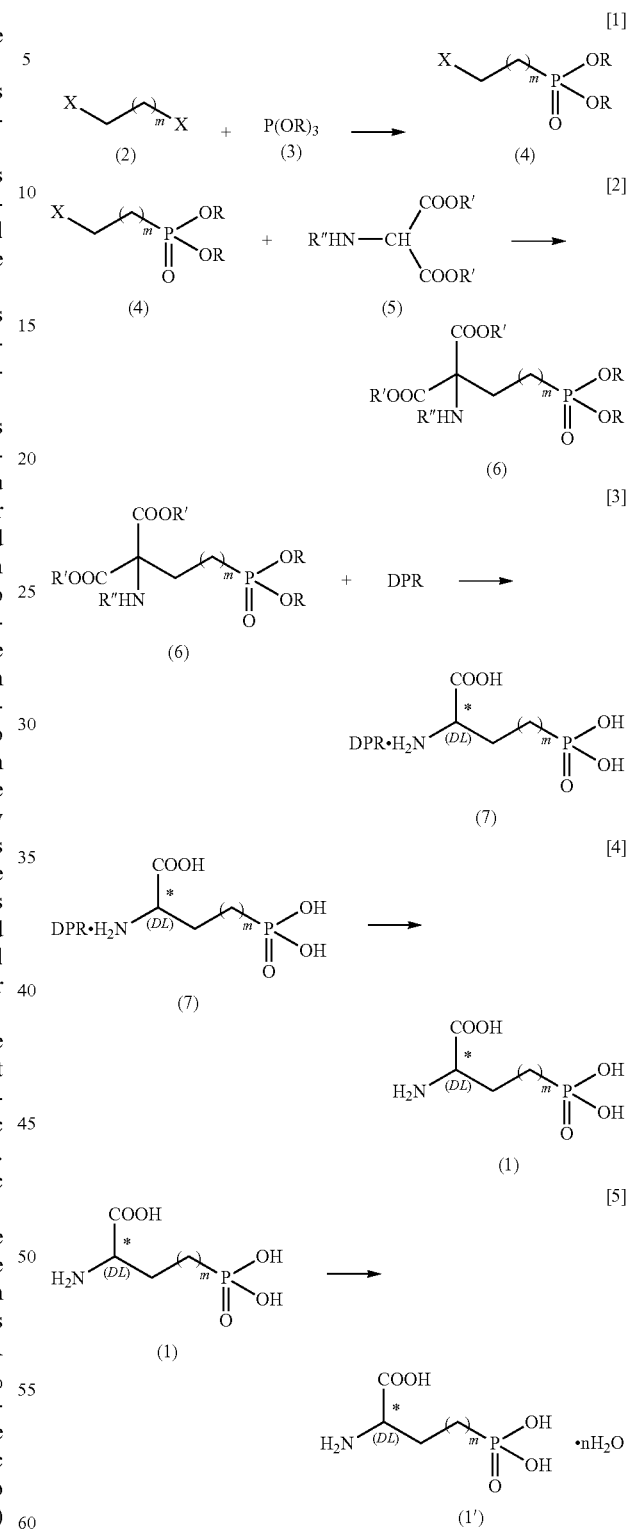

The reaction [1] is a Michaelis-Arbuzov reaction, which reacts a dihalogenated alkylene represented by Formula (2) with a phosphorous ester represented by Formula (3) to give a phosphonoalkanoic acid represented by Formula (4). The phosphorous ester represented by Formula (3) is used in an amount of typically about 0.1 to about 1.0 mole per mole of the dihalogenated alkylene represented by Formula (2).

The reaction [1] is performed at a temperature of preferably, for example, about 130° C. to about 140° C. for a time of typically about 0.5 to about 2 hours.

The reaction [2] reacts the phosphonoalkanoic acid represented by Formula (4), which is obtained through the reaction [1], with a compound represented by Formula (5) to give a compound represented by Formula (6). The compound represented by Formula (5) is used in an amount of typically about 0.7 to about 1.3 moles per mole of the phosphonoalkanoic acid represented by Formula (4).

The reaction [2] is preferably performed in the presence of a base, to effectively promotively proceed. Non-limiting examples of the base include carbonates such as potassium hydrogencarbonate, sodium hydrogencarbonate, potassium carbonate, and sodium carbonate, of which alkali metal carbonates are typified; alkali metal hydroxides such as sodium hydroxide and potassium hydroxide; alkaline earth metal hydroxides such as calcium hydroxide and magnesium hydroxide; phosphates such as sodium dihydrogenphosphate and potassium dihydrogenphosphate, of which alkali metal phosphates are typified; carboxylates such as sodium acetate and potassium acetate, of which alkali metal carboxylates are typified; organic bases such as triethylamine and pyridine; metal alkoxides such as sodium methoxide and sodium ethoxide, of which alkali metal alkoxys are typified; and metal hydrides such as sodium hydride. Each of different bases may be used alone or in combination. The base is used in an amount of typically about 0.9 to about 1.1 moles per mole of the phosphonoalkanoic acid represented by Formula (4).

The reaction [2] is preferably performed in the presence of a solvent. Examples of the solvent include, but are not limited to, ketones such as acetone and ethyl methyl ketone; ethers such as tetrahydrofuran and dioxane; nitriles such as acetonitrile; sulfoxides such as dimethyl sulfoxide; sulfones such as sulfolane; esters such as ethyl acetate; amides such as dimethylformamide; alcohols such as methanol, ethanol, and t-butyl alcohol; hydrocarbons such as pentane, hexane, and petroleum ether; aromatic hydrocarbons such as benzene, toluene, and xylene; halogen-containing compounds such as methylene chloride, chloroform, bromoform, chlorobenzene, and bromobenzene; chain carbonates such as dimethyl carbonate, diethyl carbonate, and ethyl methyl carbonate; and cyclic carbonates such as ethylene carbonate and propylene carbonate. Each of different solvents may be used alone or in combination.

The reaction [2] is performed at a temperature of preferably, for example, about 100° C. to about 110° C. for a time of typically about 6 to about 24 hours.

The reaction [3] deprotects the protected carboxy group (—COOR'), the protected amino group (—NHR"), and the protected phosphonate group (—P(=O) (OR)$_2$) in the compound represented by Formula (6), which is obtained through the reaction [2], to give a compound represented by Formula (7). The protected groups can be deprotected by reacting the compound with a deprotectant. The deprotectant (represented by "DPR" in the formulae) for use herein is advantageously selected from strong bases (such as sodium hydroxide) or strong acids (such as hydrochloric acid).

The reaction [3] is performed at a temperature of preferably, for example, about 90° C. to about 100° C. for a time of typically about 20 to about 24 hours.

The reaction [4] reacts the compound represented by Formula (7), which is obtained through the reaction [3], with a compound capable of trapping the deprotectant, to trap the deprotectant to thereby give a compound represented by Formula (1). For example, when the deprotectant is hydrochloric acid, the compound capable of trapping the deprotectant for use herein is preferably propylene oxide. The compound capable of trapping the deprotectant is used in an amount of typically about 3.0 to about 6.0 moles per mole of the compound represented by Formula (7).

A hydrate of the compound represented by Formula (1) (i.e., the compound represented by Formula (1'), where n is a number from greater than 0 to 5) can be produced by subjecting the compound represented by Formula (1), which is obtained through the reaction [4], to Step [5] (reaction [5]). Specifically, the compound represented by Formula (1') is obtained by subjecting the compound represented by Formula (1) to a crystallization treatment using water and a water-soluble solvent.

The water-soluble solvent is preferably an organic solvent that is soluble in water in any proportion at room temperature (25° C.) and preferably one having a solubility in water of 50% or more (more preferably 80% or more, and particularly preferably 95% or more).

The water-soluble solvent for use herein is preferably selected from alcohols, exemplified by $C_1$-$C_5$ lower alcohols such as methanol and ethanol.

The reactions [1] to [5] may be performed in any atmosphere harmless to the reactions, such as an air atmosphere, nitrogen atmosphere, or argon atmosphere. The reactions may be performed at normal atmospheric pressure, under reduced pressure, or under pressure (under a load). The reactions can be performed according to any system such as a batch system, semi-batch system, or continuous system.

After the completion of each of the reactions [1] to [5], the obtained reaction product may be subjected to a treatment such as filtration, washing, and/or drying (such as air drying, vacuum drying, or hot-air drying).

Method for Producing Optically Active 2-Amino-Phosphonoalkanoic Acid or Hydrate Thereof A method according to an embodiment of the present invention for producing an optically active 2-amino-phosphonoalkanoic acid or a hydrate thereof includes preparing and decomposing. In the preparing, an optically active 2-amino-phosphonoalkanoic acid salt (including a hydrate salt) is prepared by the method for producing an optically active 2-amino-phosphonoalkanoic acid salt. In the decomposing, the prepared compound is decomposed to give a corresponding optically active 2-amino-phosphonoalkanoic acid, or a hydrate thereof, having the same configuration as the compound before decomposition.

The optically active 2-amino-phosphonoalkanoic acid salt (including a hydrate salt) may be decomposed by any technique, but is preferably decomposed by a technique using an ion exchange resin (in particular, an acidic cation-exchange resin). The ion exchange resin for use herein may be selected from AMBERLITE IR-120B (trade name, supplied by ORGANO CORPORATION) and DIAION (trade name, supplied by Mitsubishi Chemical Corporation).

After the decomposition of the optically active 2-amino-phosphonoalkanoic acid salt (including a hydrate salt), the reaction product is preferably subjected to a treatment such as filtration, washing, and/or drying.

The method can give a D-AP or a hydrate thereof, or an L-AP or a hydrate thereof, each of which has a high purity (in terms of optical purity, typically 99.0% enantiomeric excess (ee) or more, preferably 99.5% ee or more, and particularly preferably 99.9% ee or more).

The present invention can give, in particular, a D-2-amino-phosphonoalkanoic acid hydrate represented by Formula (1-1'), or an L-2-amino-phosphonoalkanoic acid hydrate represented by Formula (1-2'), efficiently with high purity, where Formulae (1-1') and (1-2') are expressed as follows:

[Chem. 15]

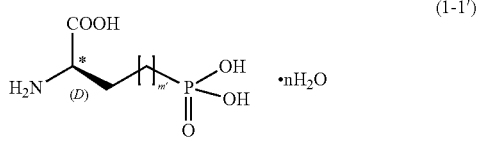

(1-1')

wherein m' represents 1, 3, or 5; n represents a number from greater than 0 to 5; and the asterisk marks an asymmetric atom,

[Chem. 16]

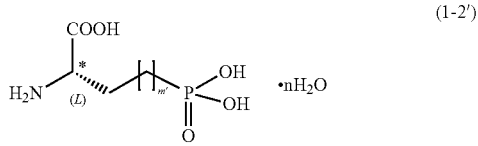

(1-2')

wherein m' represents 1, 3, or 5; n represents a number from greater than 0 to 5; and the asterisk marks an asymmetric atom.

Optically Active Substance, Salt Between Optically Active Substance and Optically Active Basic Compound The optically active 2-amino-phosphonoalkanoic acid salts (including hydrates) and the optically active 2-amino-phosphonoalkanoic acids (including hydrates), which are obtained by the methods, have approximately no deliquescency and crystallize at room temperature. The compounds are storable excellently stably, are stable over 6 months or longer (in particular, 24 months or longer) in environments at room temperature and relative humidity of 75%, and are easy to handle. The compounds also have pharmacological activities comparable to or superior to those of Nahlsgen (registered trademark). For example, the optically active 2-amino-phosphonoalkanoic acid salts (including hydrates) and the optically active 2-amino-phosphonoalkanoic acids (including hydrates), when administered (about 10 µM) to human skin fibroblasts, can effectively promote or accelerate production of collagen. The compounds, which accelerate the collagen production concentration-dependently, do not accelerate the collagen production unlimitedly when administered in excess. The compounds can exert effects or activities such as elastin production promoting activity, heat-shock protein 47 (HSP47) production promoting activity, glutathione production promoting activity, fillagrin production promoting activity, fillagrin gene expression enhancement effect, promoting activity on migration and/or growth of epidermic keratinocytes, and wound healing promoting activity. Further, the compounds have approximately no cytotoxicity and are highly safe. The compounds are advantageously usable typically as collagen production promoters, elastin production promoters, HSP47 production promoters, glutathione production promoters, fillagrin production promoters, fillagrin gene expression enhancers, and epidermic keratinocyte migration-growth stimulators. The compounds are also advantageously usable typically as healing promoters for mucosa such as oral mucosa and ocular mucosa, for the treatment and/or prophylaxis of oral mucosal diseases such as periodontal diseases, and ocular mucosal diseases such as conjunctivitis.

The optically active 2-amino-phosphonoalkanoic acid salts (including hydrates) and the optically active 2-amino-phosphonoalkanoic acids (including hydrates) are suitable for uses for health and beauty of the skin and/or hair. Also, the compounds are advantageously usable for the treatment and/or prophylaxis against various diseases involved in, or mediated by, collagen, elastin, HSP47, glutathione, fillagrin, and migration and/or growth of epidermic keratinocytes.

The optically active 2-amino-phosphonoalkanoic acid salts (including hydrates) and the optically active 2-amino-phosphonoalkanoic acids (including hydrates), when applied to epidermal tissues (such as skin, hair, and nails), are effective to promote or enhance collagen production and to give better barrier functions. The compounds are advantageously usable typically for the treatment and/or prophylaxis of skin diseases such as allergic skin diseases, ichthyosis vulgaris, and senile xerosis. The optically active 2-amino-phosphonoalkanoic acid salts (including hydrates) and the optically active 2-amino-phosphonoalkanoic acids (including hydrates), when applied to the skin, accelerate glutathione production and/or fillagrin production and are efficacious for anti-aging and/or skin-whitening. Thus, the compounds are advantageously usable as additives typically to cosmetics for skin care use.

The cosmetics for skin care use are exemplified by, but not limited to, makeup cosmetics such as foundation, eye shadow, mascara, eyebrow pencil or paint, cheek rouge, lipsticks, and manicure; and skin-care cosmetics such as lotions, milky lotions, and beauty essence.

The optically active 2-amino-phosphonoalkanoic acid salts (including hydrates) and the optically active 2-amino-phosphonoalkanoic acids (including hydrates) may be used in amounts adjusted appropriately according to the intended use. For example, each compound, when added to a cosmetic, may be used in an amount within such a range as to give a concentration of typically 0.5 to 70 µM, preferably 10 to 60 µM, particularly preferably 30 to 60 µM, and most preferably 40 to 60 µM.

EXAMPLES

The present invention will be illustrated in further detail with reference to several examples below. It should be noted, however, that the examples are by no means intended to limit the scope of the present invention. In the following formulae, each of the asterisks marks an asymmetric atom.

Preparation Example 1: Preparation of DL-2-Amino-4-Phosphonobutanoic Acid Hydrate

[Chem. 17]

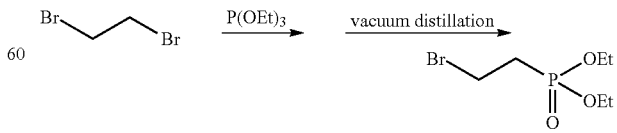

Triethyl phosphite (40.0 ml, 233 mmol) was added to 1,2-dibromoethane (80 ml, 928 mmol), the mixture was raised in temperature up to 140° C. with stirring on an oil bath, heated at the same temperature for 30 minutes, and naturally cooled. After cooling down to around 40° C., pressure reduction was started. The pressure reduction and heating were gradually intensified, to distill off excess dibromoethane and by-products such as ethyl bromide. The pressure reduction was then further intensified to a degree of vacuum of about 1 mmHg, and distillation was performed with heating at about 130° C. This gave colorless, odorless, oily diethyl 2-bromoethylphosphonate (36.3 g, yield: 64%).

[Chem. 18]

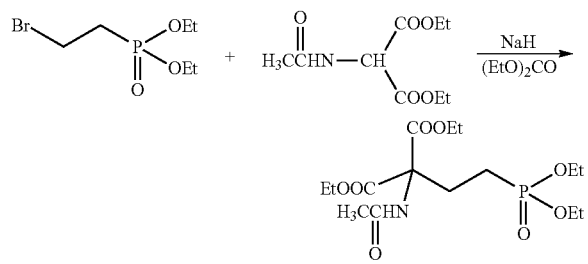

Diethyl 2-bromoethylphosphonate (25.0 g, 102 mmol) was combined with toluene (70 mL), diethyl carbonate (40 mL), diethyl acetamidomalonate (16.9 g, 77.6 mmol), and 60% sodium hydride (4.40 g, 110 mmol) washed with hexane, followed by refluxing at 110° C. After being refluxed for 24 hours, the mixture was cooled down to room temperature, filtered through Celite to remove solids, and the filtrate was concentrated under vacuum. This gave brown, oily diethyl 2-acetamido-2-[2-(diethoxyphosphoryl)ethyl]malonate (33.3 g, in quantitative yield).

[Chem. 19]

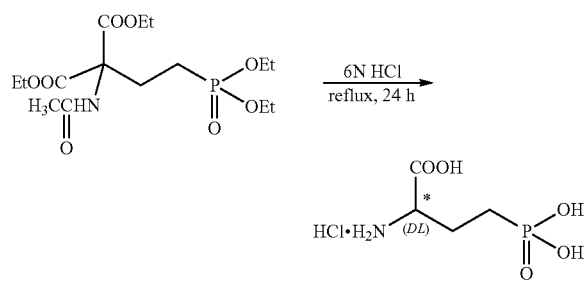

Diethyl 2-acetamido-2-[2-(diethoxyphosphoryl)ethyl]malonate (33.3 g, 87.3 mmol) was dissolved in 6 N hydrochloric acid (154 mL) and refluxed for 24 hours. The resulting substance was concentrated under vacuum and yielded brown oily DL-2-amino-4-phosphonobutanoic acid hydrochloride (21.1 g, in quantitative yield).

[Chem. 20]

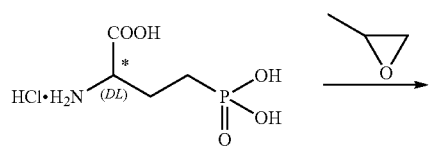

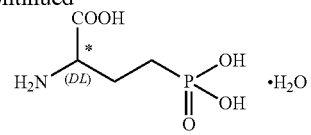

DL-2-Amino-4-phosphonobutanoic acid hydrochloride (21.1 g, 96.1 mmol) was dissolved in water (30 mL). The resulting solution with vigorous stirring and cooling at 5° C. to 10° C. was combined with propylene oxide (30 mL, 428 mmol) added dropwise and, simultaneously, ethanol (150 mL) added gradually dropwise, and the mixture was stirred at room temperature for 4 days. The precipitated crystals were collected by filtration, washed with ethanol, and dried at 40° C. under reduced pressure. This gave colorless powdery DL-2-amino-4-phosphonobutanoic acid monohydrate (11.8 g, yield: 61.1%). The thermal analysis results of this compound are presented in FIG. 1.

Mp (DSC): 115.3° C., 203.1° C. (dec).
IR (cm$^{-1}$): 3147, 2981, 2287, 1704, 1637, 1524, 1834, 1103, 1024, 895.

Preparation Example 2

DL-2-Amino-5-phosphonopentanoic acid was prepared by a procedure similar to that in Preparation Example 1, except for using 1,3-dibromopropane as a starting material instead of 1,2-dibromoethane.

Preparation Example 3

Figure 2:
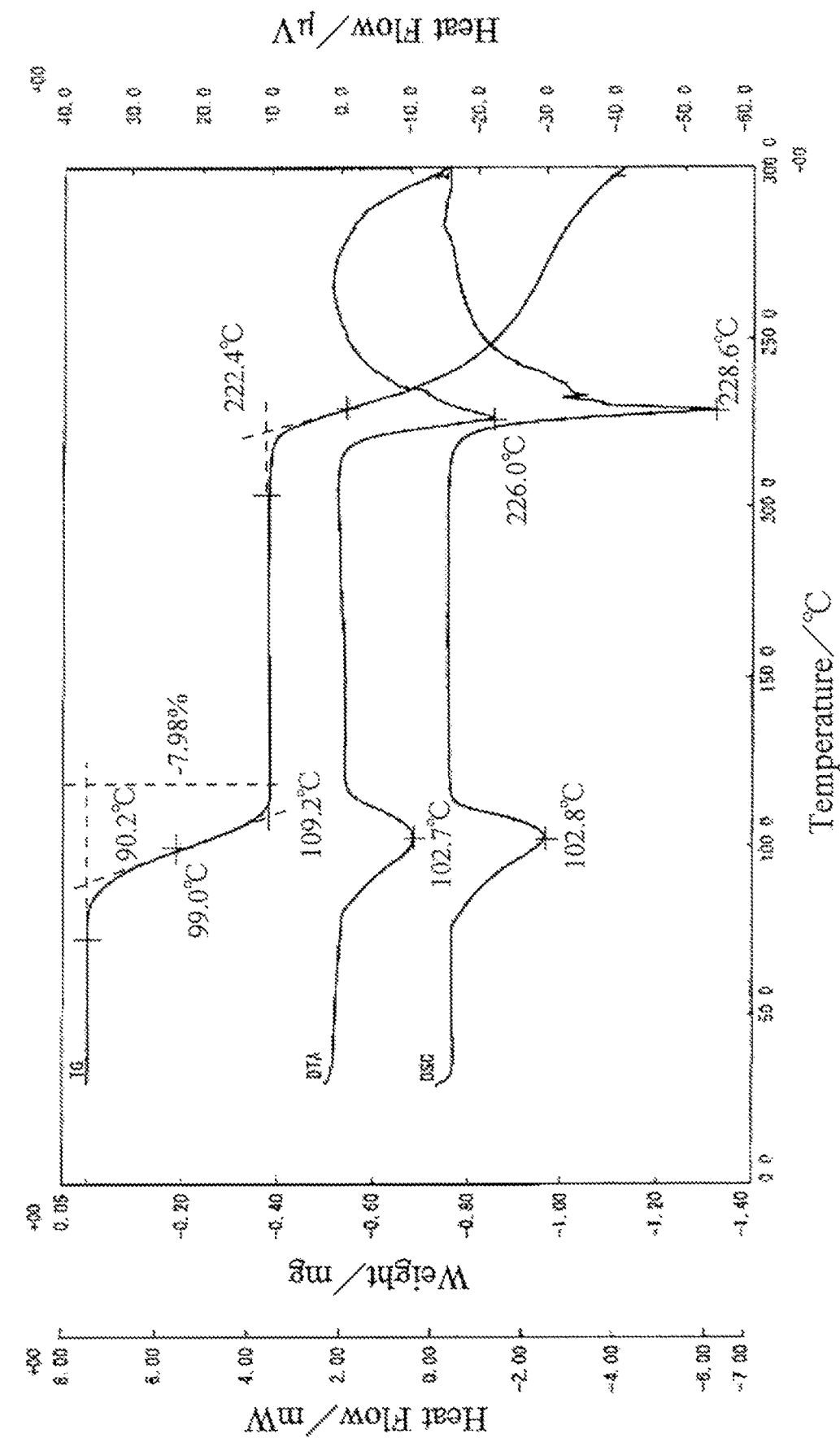
FIG. 2 is a chart illustrating thermal analysis results of DL-2-amino-6-phosphonohexanoic acid monohydrate prepared in Preparation Example 3.

DL-2-Amino-6-phosphonohexanoic acid monohydrate was prepared by a procedure similar to that in Preparation Example 1, except for using 1,4-dibromobutane as a starting material instead of 1,2-dibromoethane. The thermal analysis results of the obtained compound are presented in FIG. 2.

Preparation Example 4

DL-2-Amino-7-phosphonoheptanoic acid was prepared by a procedure similar to that in Preparation Example 1, except for using 1,5-dibromopentane as a starting material instead of 1,2-dibromoethane.

Preparation Example 5

Figure 3:
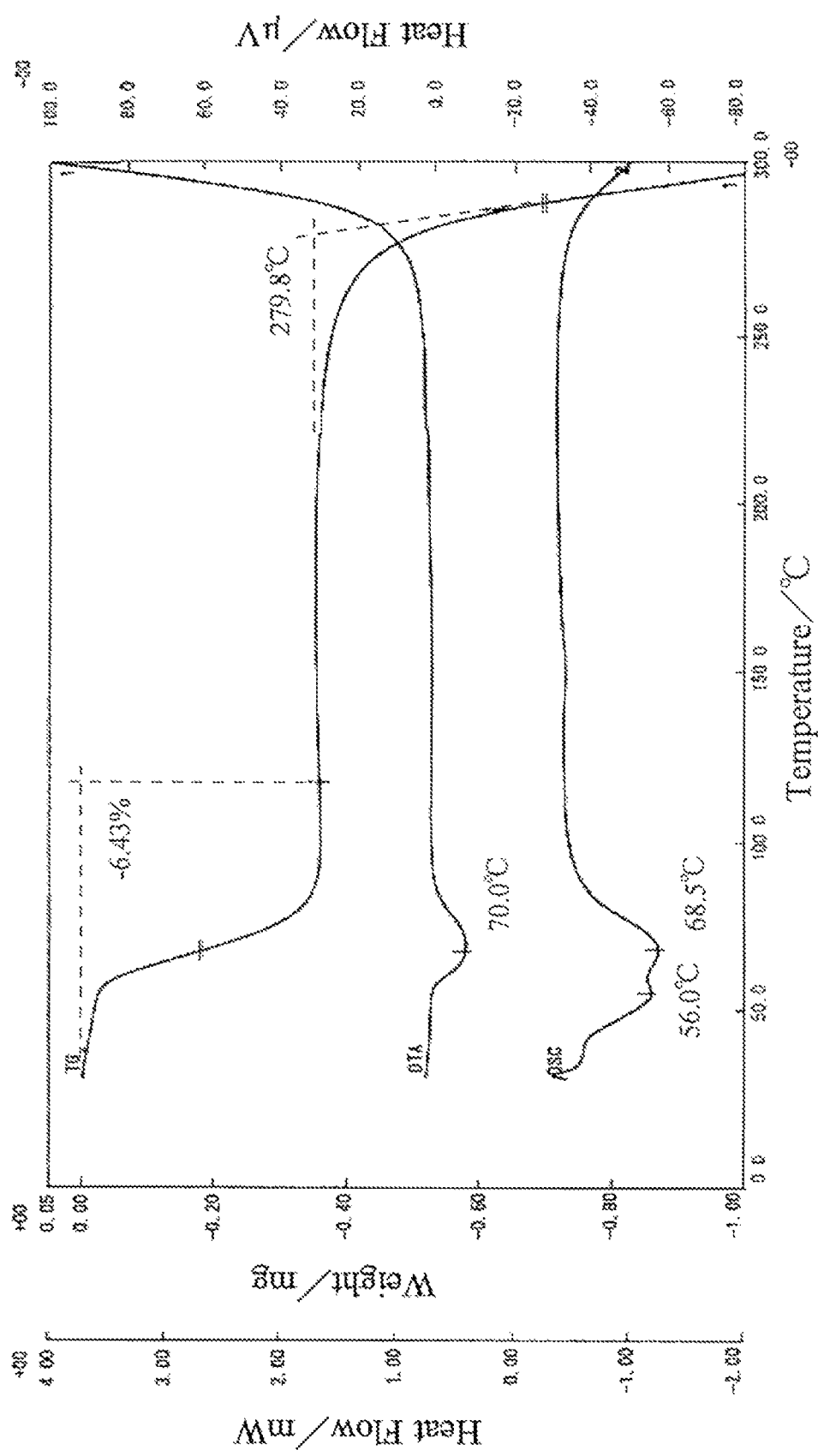
FIG. 3 is a chart illustrating thermal analysis results of DL-2-amino-8-phosphonooctanoic acid monohydrate prepared in Preparation Example 5.

DL-2-Amino-8-phosphonooctanoic acid monohydrate was prepared by a procedure similar to that in Preparation Example 1, except for using 1,6-dibromohexane as a starting material instead of 1,2-dibromoethane. The thermal analysis results of the obtained compound are presented in FIG. 3.

Preparation Example 6

DL-2-Amino-9-phosphonononanoic acid (2.5 g) was prepared by a procedure similar to that in Preparation Example 1, except for using 1,7-dibromoheptane (25.0 g, 97 mmol) as a starting material instead of 1,2-dibromoethane.

Mp (DSC): 221° C. (dec)
IR (cm$^{-1}$): 3300-2000 (br), 2917, 2848, 1715, 1525, 1415, 1266, 1088, 1052, 779, 720, 642.
$^1$H-NMR (600 MHz, D$_2$O with DCl) $\delta_H$: 1.15-1.33 (8H, m), 1.37-1.44 (2H, m), 1.57-1.67 (2H, m), 1.73-1.86 (2H, m), 3.94 (1H, t).
$^{31}$P-NMR (242 MHz, D$_2$O with DCl) $\delta_P$: 33.8.
HRMS (FAB) calcd for C$_9$H$_{20}$NO$_5$P (M+H) 253, 1079: Found 254, 1155.

Preparation Example 7

Figure 4:
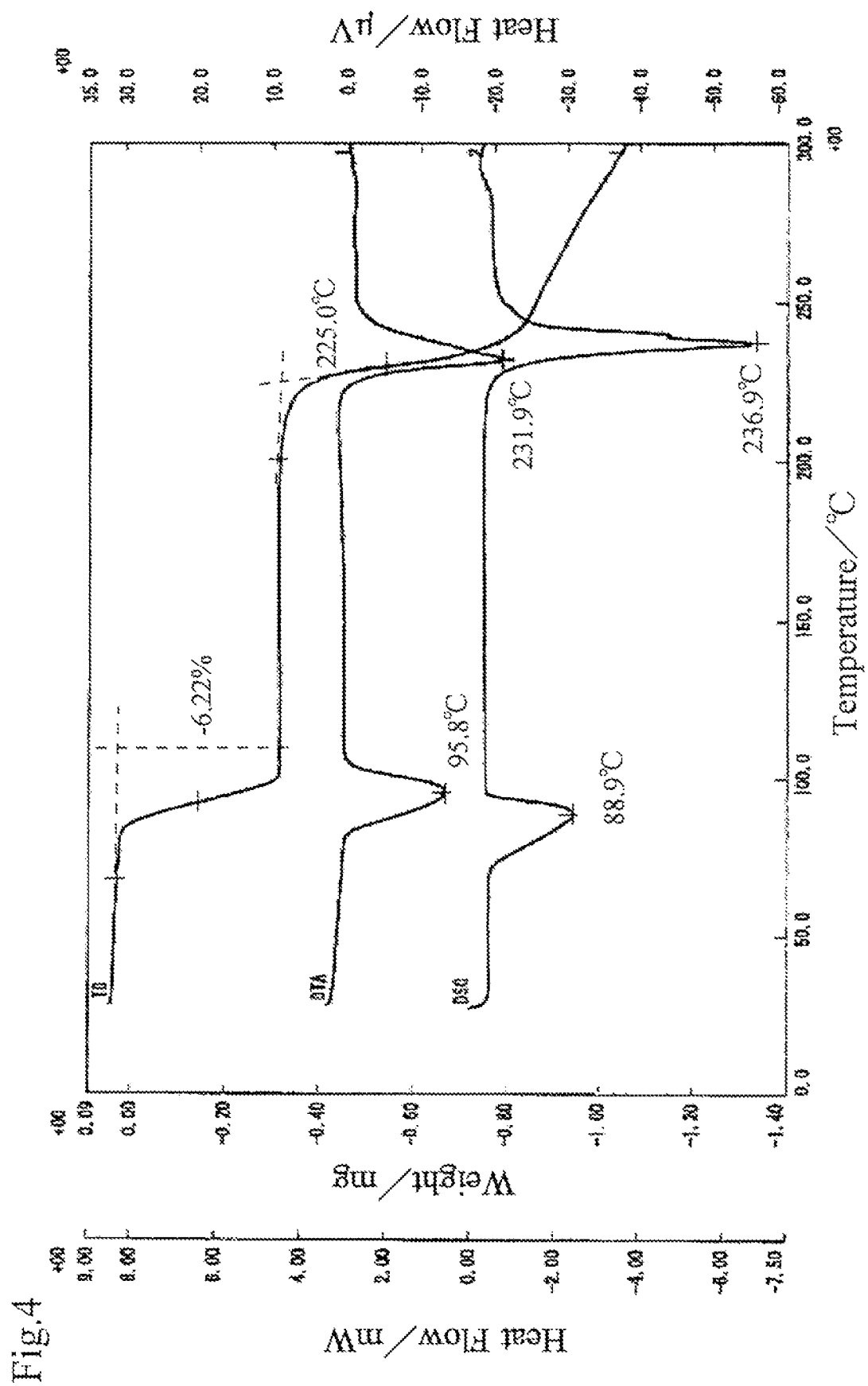
FIG. 4 is a chart illustrating thermal analysis results of DL-2-amino-10-phosphonodecanoic acid monohydrate prepared in Preparation Example 7.

DL-2-Amino-10-phosphonodecanoic acid monohydrate (1.8 g) was prepared by a procedure similar to that in Preparation Example 1, except for using 1,8-dibromooctane (15.5 g, 57 mmol) as a starting material instead of 1,2-dibromoethane. The thermal analysis results of the obtained compound are presented in FIG. 4.

Mp (DSC): 237° C. (dec)

IR (cm$^{-1}$): 3300-2000 (br), 2918, 2848, 1715, 1621, 1581, 1515, 1466, 1416, 1245, 1014, 927, 821, 776, 716.

$^1$H-NMR (600 MHz, D$_2$O with DCl) $\delta_H$: 0.95-1.13 (10H, m), 1.16-1.23 (2H, m), 1.42-1.47 (2H, m), 1.52-1.65 (2H, m), 3.75 (1H, t).

$^{31}$P-NMR (242 MHz, D$_2$O with DCl) $\delta_P$: 34.0.

HRMS (FAB) calcd for C$_{10}$H$_{22}$NO$_5$P (M+H) 267, 1236: Found 268, 1315.

Example 1: Optical Resolution of DL-2-Amino-4-Phosphonobutanoic Acid

DL-2-Amino-4-phosphonobutanoic acid monohydrate (50 mg, 0.248 mmol), which was prepared in the preparation example, was combined with each of the optically active basic compounds (0.300 mmol) and corresponding solvents given in Table 1, followed by dissolution with heating. The precipitated crystals were collected by filtration, washed, and dried. This gave a series of diastereomeric salts. These diastereomeric salts were analyzed by chiral HPLC to determine their optical purities (de (%)). The results are presented in Table 1 below.

crude crystals. $[\alpha]_D^{20}$ +6.3 (c1, H$_2$O), 89.3% de (under the chiral HPLC analysis conditions given with Table 1)

The crude crystals of D-2-amino-4-phosphonobutanoic acid L-Arg salt (4.30 g) were combined with water (43 mL), heated to 70° C. with stirring, and further combined with methanol (43 mL) added dropwise. The mixture was slowly cooled, stirred at 20° C. for 3 hours, and the precipitated crystals were collected by filtration, washed, and dried. This gave recrystallized crystals (1) of D-2-amino-4-phosphonobutanoic acid L-Arg salt (3.62 g). $[\alpha]_D^{20}$ +6.3 (c1, H$_2$O), 98.3% de The recrystallized crystals (1) of D-2-amino-4-phosphonobutanoic acid L-Arg salt (3.50 g) were combined with water (35 mL), heated to 70° C. with stirring, and further combined with methanol (35 mL) added dropwise at the same temperature. The mixture was slowly cooled and then stirred at 10° C. for 2 hours. The precipitated crystals were collected by filtration, washed, and dried. This gave recrystallized crystals (2) of D-2-amino-4-phosphonobutanoic acid L-Arg salt (3.35 g).

Mp (DSC): 263° C. (dec), $[\alpha]_D^{20}$ +6.5 (c1, H$_2$O), 100% de (under the chiral HPLC analysis conditions given with Table 1) IR (cm$^{-1}$): 3355, 2945, 2084, 1663, 1581, 1412, 1338, 1162, 984, 780, 687.

$^1$H-NMR (600 MHz, D$_2$O) $\delta_H$: 1.57-1.74 (4H, m), 1.84-1.93 (2H, m), 2.02-2.14 (2H, m), 3.22 (2H, dd, J$_{H-H}$=6.9 and 6.9 Hz), 3.75 (1H, dd, J$_{H-H}$=6.2 and 6.2 Hz), 3.78 (1H, dd, J$_{H-H}$=6.5 and 5.5 Hz).

$^{31}$P-NMR (121 MHz, D$_2$O) $\delta_P$: 23.7.

The recrystallized crystals (2) of D-2-amino-4-phosphonobutanoic acid L-Arg salt (2.35 g) were dissolved in pure water, and the solution was slowly passed through an ion exchange resin AMBERLITE IR-120 (H$^+$) (trade name,

TABLE 1

| | | Diastereomeric salt | | |
|---|---|---|---|---|
| Optically active basic compound | Solvent (mL) | 2-Amino-4-phosphonobutanoic acid to form the salt | Yield (mg) | de (%) |
| Cinchonine | Methanol (0.3) | L form | 12.3 | 74 |
| Quinidine | Methanol (0.3) | D form | 30.4 | 90 |
| Cinchonidine | Methanol (0.5)/Ethanol (0.1) | D form | 81.8 | 24 |
| L-Arginine | Methanol (1.5)/Water (1.55) | D form | 20.3 | 99 |
| D-HPGH | Methanol (1.2)/Water (0.4) | D form | 42.3 | 31 |
| D-Phenylalaninamide | 2-Propanol (1.2)/Water (0.15) | D form | 8 | 47 |
| L-Ornithine | Methanol (1.0)/Water (1.1) | L form | 13 | 20 |

D-HPGH: D-p-Hydroxyphenylglycine hydrazide
Chiral HPLC analysis conditions:
Column: SUMICHIRAL OA-5000 (4.6 in diameter by 150 mm)
Mobile phase: 2 mM-CuSO$_4$ in water, Flow rate: 1.0 ml/min,
Detector: UV-254 nm, Temp. 40° C., Sample: 2-3 mg/10 ml buffer, 5 μl

Example 2: Optical Resolution of DL-2-Amino-4-Phosphonobutanoic Acid Using L-Arg DL-2-Amino-4-phosphonobutanoic acid monohydrate (5.00 g, 24.9 mmol), which was prepared in the preparation example, and L-Arg (4.99 g, 28.6 mmol) were dissolved in water (50 mL) with heating, the solution was combined with methanol (65 mL) added gradually at 70° C., the mixture was slowly cooled, and stirred at 25° C. for 3 hours. The precipitated crystals were collected by filtration (the filtration mother liquor was used later as "filtration mother liquor*"), washed, and dried. This gave D-2-amino-4-phosphonobutanoic acid L-Arg salt (4.41 g) as colorless supplied by ORGANO CORPORATION) (10.4 mL). After the resin was washed with pure water (300 mL), the passed liquid and the washings were combined and concentrated. The residual solids were combined with and dispersed in methanol (10 mL), collected by filtration, washed with methanol, and dried. This gave colorless crystals of D-2-amino-4-phosphonobutanoic acid monohydrate (1.19 g).

Mp (DSC): 98.0° C., 211.0° C. (dec), $[\alpha]_D^{20}$ −17.3 (c1, H$_2$O), 100% ee IR (cm$^{-1}$): 3247, 2642, 1723, 1520, 1265, 984, 923, 731.

$^1$H-NMR (300 MHz, D$_2$O) $\delta_H$: 1.58-1.86 (2H, m), 2.02-2.25 (2H, m), 4.00-4.06 (1H, dd, J$_{H-H}$=6.2 and 6.2 Hz).

$^{31}$P-NMR (121 MHz, D$_2$O) $\delta_P$: 24.6.

The filtration mother liquor* obtained above was concentrated, the residue was combined with and dissolved in pure water, and the solution was slowly passed through an ion exchange resin AMBERLITE IR-120 (H+) (trade name, supplied by ORGANO CORPORATION) (25 mL). After the resin was washed with about 300 mL of pure water, the passed liquid and the washings were combined, concentrated, and the residue was dried. This gave colorless crude crystals of L-2-amino-4-phosphonobutanoic acid monohydrate (2.37 g; 89.0% ee).

The crude crystals of L-2-amino-4-phosphonobutanoic acid monohydrate (2.30 g) and D-Arg (2.23 g) were dissolved in water (45 mL) with heating, the solution was combined with methanol (45 mL) added gradually at 70° C., the mixture was slowly cooled, and stirred at 15° C. for 2 hours. The precipitated crystals were collected by filtration, washed, and dried. This gave colorless, recrystallized crystals (1) of L-2-amino-4-phosphonobutanoic acid D-Arg salt (3.34 g).

Mp (DSC): 263° C. (dec), $[\alpha]_D^{20}$ −6.5 (c1, $H_2O$), 100% de

IR ($cm^{-1}$): 3355, 2945, 2084, 1663, 1581, 1413, 1338, 1162, 984, 780, 687.

$^1$H-NMR (600 MHz, $D_2O$) $\delta_H$: 1.57-1.74 (4H, m), 1.84-1.93 (2H, m), 2.02-2.14 (2H, m), 3.22 (2H, dd, $J_{H-H}$=6.9 and 6.9 Hz), 3.75 (1H, dd, $J_{H-H}$=6.2 and 6.2 Hz), 3.78 (1H, dd, $J_{H-H}$=6.5 and 5.5 Hz). $^{31}$P-NMR (121 MHz, $D_2O$) $\delta_P$: 23.7.

Figure 5:
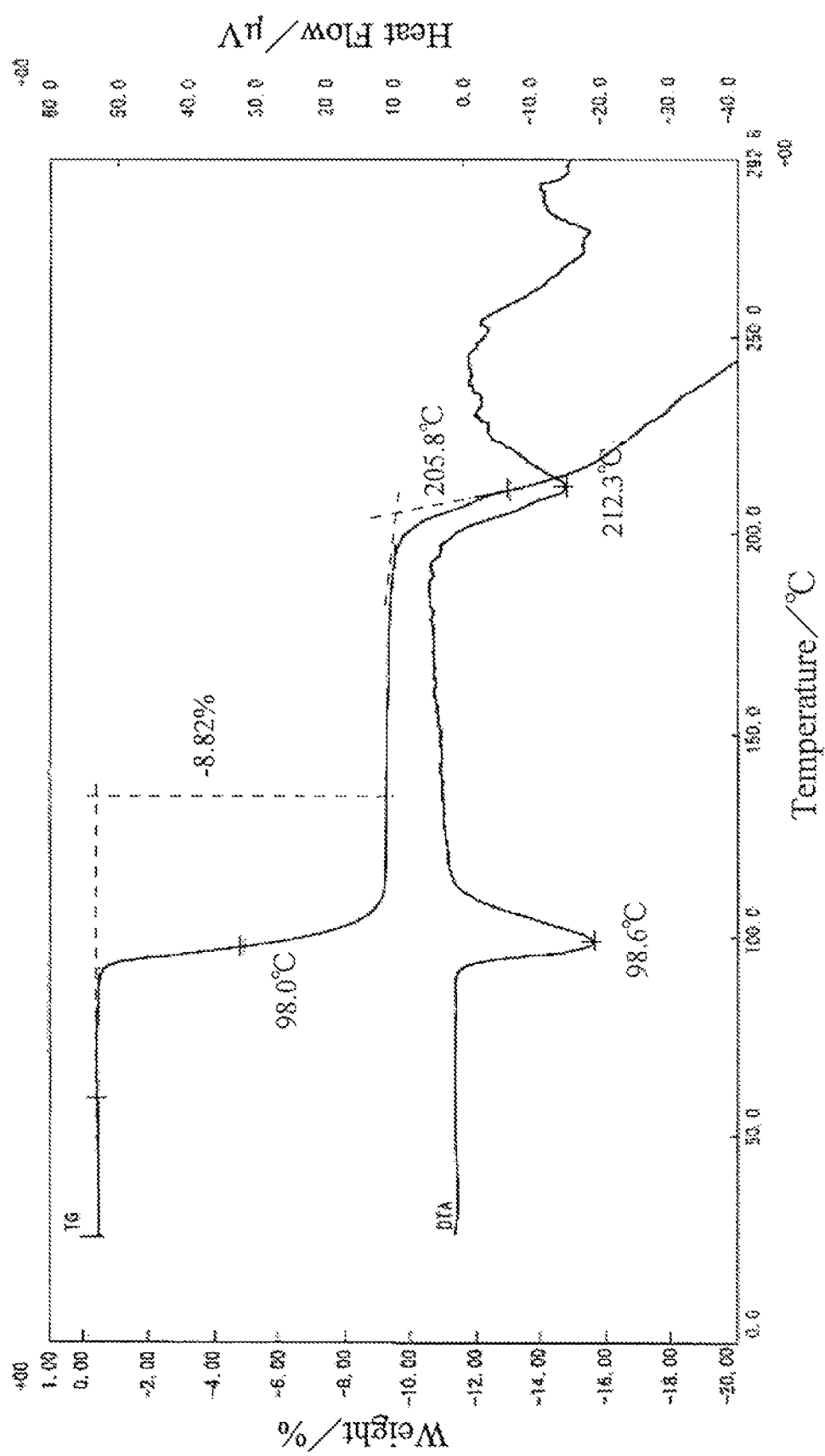
FIG. 5 is a chart illustrating thermal analysis results of L-2-amino-4-phosphonobutanoic acid monohydrate obtained in Example 2.

The recrystallized crystals (1) of L-2-amino-4-phosphonobutanoic acid D-Arg salt (2.07 g) were dissolved in pure water, and the solution was slowly passed through an ion exchange resin AMBERLITE IR-120 (H+) (trade name, supplied by ORGANO CORPORATION) (9.2 mL). After the resin was washed with pure water (300 mL), the passed liquid and the washings were combined, concentrated, the residual solids were combined with and dispersed in 10 mL of methanol, collected by filtration, washed with methanol, and dried at 40° C. under reduced pressure for 3 hours. This gave colorless crystals of L-2-amino-4-phosphonobutanoic acid monohydrate (1.07 g). The thermal analysis results of the obtained compound are presented in FIG. 5.

Mp (DSC): 98.6° C., 212.3° C. (dec), $[\alpha]_D^{20}$ +17.5 (c1, $H_2O$), 100% ee.

IR ($cm^{-1}$): 3130, 2481, 1722, 1521, 1167, 895, 718.

$^1$H-NMR (300 MHz, $D_2O$) $\delta_H$: 1.60-1.89 (2H, m), 2.02-2.28 (2H, m), 4.02-4.08 (1H, dd, $J_{H-H}$=6.2 and 6.2 Hz). $^{31}$P-NMR (121 MHz, $D_2O$) $\delta_P$: 24.6.

Example 3: Preparation of
D-2-Amino-4-Phosphonobutanoic Acid D-Arg Salt Monohydrate D-2-Amino-4-phosphonobutanoic acid monohydrate (0.165 g, 82.0 mmol) and D-Arg (0.147 g, 84.5 mmol) were dissolved in water (5 mL) with heating, concentrated under vacuum, combined with methanol (2.5 mL) added gradually, and left stand under ice cooling for 30 minutes. The precipitated crystals were collected by filtration, washed, and dried. This gave colorless crude crystals of D-2-amino-4-phosphonobutanoic acid D-Arg salt monohydrate (0.295 g).

$[\alpha]_D^{20}$ −8.2 (c1, $H_2O$)

IR ($cm^{-1}$): 3357, 2949, 2874, 2618, 1578, 1514, 1338, 1162, 1134, 1017, 663.

Example 4: Preparation of
L-2-Amino-4-Phosphonobutanoic Acid L-Arg Salt Monohydrate L-2-Amino-4-phosphonobutanoic acid monohydrate (0.165 g, 82.0 mmol) and L-Arg (0.147 g, 84.5 mmol) were dissolved in water (5 mL) with heating, concentrated under vacuum, combined with methanol (2.5 mL) added gradually, and left stand under ice cooling for 30 minutes. The precipitated crystals were collected by filtration, washed, and dried. This gave colorless crude crystals of L-2-amino-4-phosphonobutanoic acid L-Arg salt monohydrate (0.295 g).

$[\alpha]_D^{20}$ +7.8 (c1, $H_2O$)

IR ($cm^{-1}$): 3355, 2932, 1657, 1576, 1514, 1404, 1133, 1018, 895, 766, 683.

Example 5: Optical Resolution of
DL-2-Amino-6-Phosphonohexanoic Acid

DL-2-Amino-6-phosphonohexanoic acid monohydrate (50 mg), which was prepared in the preparation example, was combined with each of the optically active basic compounds (0.222 mmol) and corresponding solvents given in Table 2, followed by dissolution with heating. The precipitated crystals were collected by filtration, washed, and dried. This gave a series of diastereomeric salts. These diastereomeric salts were analyzed by chiral HPLC to determine their optical purities (de (%)). The results are presented in Table 2.

TABLE 2

| Optically active basic compound | Solvent (mL) | Diastereomeric salt 2-Amino-6-phosphonohexanoic acid to form the salt | Yield (mg) | de (%) |
|---|---|---|---|---|
| L-Tyrosine hydrazide | Water (0.5)/Methanol (2.0) | D form | 27.2 | 74 |
| (R)-1-Phenylpropylamine | Water (0.3)/Methanol (1.0) | L form | 11.4 | 96 |
| L-Valinol | Water (0.4)/Methanol (1.0) | L form | 13.9 | 70 |
| D-HPGM | Water (0.7)/Methanol (1.5) | L form | 1.4 | 98 |
| D-Phenylalanine amide | Water (0.15)/Methanol (1.0) | L form | 12.4 | 68 |
| D-HPGH | Water (1.0)/Methanol (1.5) | L form | 10 | 87 |
| D-HPGE | Water (0.1)/Methanol (1.0) | L form | 35.6 | 40 |

D-HPGM: D-p-Hydroxyphenylglycine methyl ester
D-HPGH: D-p-Hydroxyphenylglycine hydrazide
D-HPGE: D-p-Hydroxyphenylglycine ethyl ester
Chiral HPLC measurement conditions:
Column: SUMICHIRAL OA-5000 (4.6 in diameter by 150 mm)
Mobile phase: 2 mM-$CuSO_4/H_2O$:IPA = 98:2, Flow rate: 1.0 ml/min
Detector: UV-254 nm, Temp. 40° C., Sample: 5 mg/10 ml buffer, 10 μl

Example 6: Optical Resolution of DL-2-Amino-6-Phosphonohexanoic Acid Using D-HPGM DL-2-Amino-6-phosphonohexanoic acid monohydrate (5.00 g), which was prepared in the preparation example, and D-HPGM (4.38 g) were dissolved in water (55 mL) with heating, the solution was combined with methanol (100 mL) added gradually at 70° C., slowly cooled, and stirred at 25° C. for 3 hours. The precipitated crystals were collected by filtration (the filtration mother liquor was used later as "filtration mother liquid*"), washed, and dried. This gave colorless crude crystals of L-2-amino-6-phosphonohexanoic acid D-HPGM salt monohydrate (3.24 g).

$[\alpha]_D^{26}$ −64.6 (c1, $H_2O$), 92.1% de (under the chiral HPLC analysis conditions given with Table 2)

The crude crystals of L-2-amino-6-phosphonohexanoic acid D-HPGM salt monohydrate, (3.20 g) were combined with water (19.2 mL), heated up to 75° C. with stirring, and further combined with methanol (80 mL) added dropwise. The mixture was slowly cooled, stirred at 15° C. for 3 hours, the precipitated crystals were then filtered, washed, and dried. This gave recrystallized crystals (1) of L-2-amino-6-phosphonohexanoic acid D-HPGM salt monohydrate (2.60 g).

Mp (DSC): 116.6° C., 205.4° C. (dec), $[\alpha]_D^{25}$ −65.0 (c1, $H_2O$), 100% de IR ($cm^{-1}$): 3463, 2860, 2644, 1733, 1605, 1524, 1579, 1418, 1253, 998, 894.

$^1$H-NMR (600 MHz, $D_2O$) $\delta_H$: 1.43-1.54 (2H, m), 1.56-1.65 (4H, m), 1.83-1.96 (2H, m), 3.76 (1H, dd, $J_{H-H}$=7.2 and 5.1 Hz), 3.84 (3H, s), 5.23 (1H, s), 6.99 (2H, d, $J_{H-H}$=8.6 Hz), 7.36 (2H, d, $J_{H-H}$=8.6 Hz). $^{31}$P-NMR (121 MHz, $D_2O$) $\delta_P$: 26.8.

The recrystallized crystals (1) of L-2-amino-6-phosphonohexanoic acid D-HPGM salt monohydrate (2.50 g) were dissolved in pure water, and the solution was slowly passed through an ion exchange resin AMBERLITE IR-120 (H+) (trade name, supplied by ORGANO CORPORATION) (10 mL). After the resin was thoroughly washed with pure water, the passed liquid and the washings were combined and concentrated. The residual solids were combined with and dispersed in methanol (15 mL), collected by filtration, washed with methanol, and dried. This gave colorless crystals of L-2-amino-6-phosphonohexanoic acid monohydrate (1.29 g).

Mp (DSC): 93.8° C., 224.7° C., 225° C. (dec), $[\alpha]_D^{25}$ +19.7 (c1, 2N—HCl), 100% ee IR ($cm^{-1}$): 3235, 2933, 1704, 1600, 1537, 1148, 998, 878, 770.

$^1$H-NMR (600 MHz, $D_2O$+DCl) $\delta_H$: 1.42-1.62 (4H, m), 1.74-1.80 (2H, m), 1.85-1.91 (1H, m), 1.93-1.99 (1H, m), 4.05 (1H, dd, $J_{H-H}$=6.4 and 6.4 Hz). $^{31}$P-NMR (121 MHz, $D_2O$) $\delta_P$: 32.6.

The filtration mother liquor* obtained above was concentrated, the residue was combined with and dissolved in pure water, and the solution was slowly passed through an ion exchange resin AMBERLITE IR-120 (H+) (trade name, supplied by ORGANO CORPORATION) (25 mL). After the resin was thoroughly washed with pure water, the passed liquid and the washings were combined and concentrated, and the residue was dried. This gave white crude crystals of D-2-amino-6-phosphonohexanoic acid monohydrate (3.17 g). $[\alpha]_D^{26}$ −6.5 (c1, $H_2O$), 60.8% ee The crude crystals of D-2-amino-6-phosphonohexanoic acid monohydrate (3.10 g) and L-HPGM (2.71 g) were dissolved in water (34.5 mL) with heating, the solution was combined with methanol (144 mL) added gradually at 70° C., slowly cooled, and stirred at 15° C. for 2 hours. The precipitated crystals were collected by filtration, washed, and dried. This gave colorless, crude crystals (1) of D-2-amino-6-phosphonohexanoic acid L-HPGM salt monohydrate (3.30 g).

$[\alpha]_D^{25}$ +64.9 (c1, $H_2O$), 96.5% de.

Figure 6:
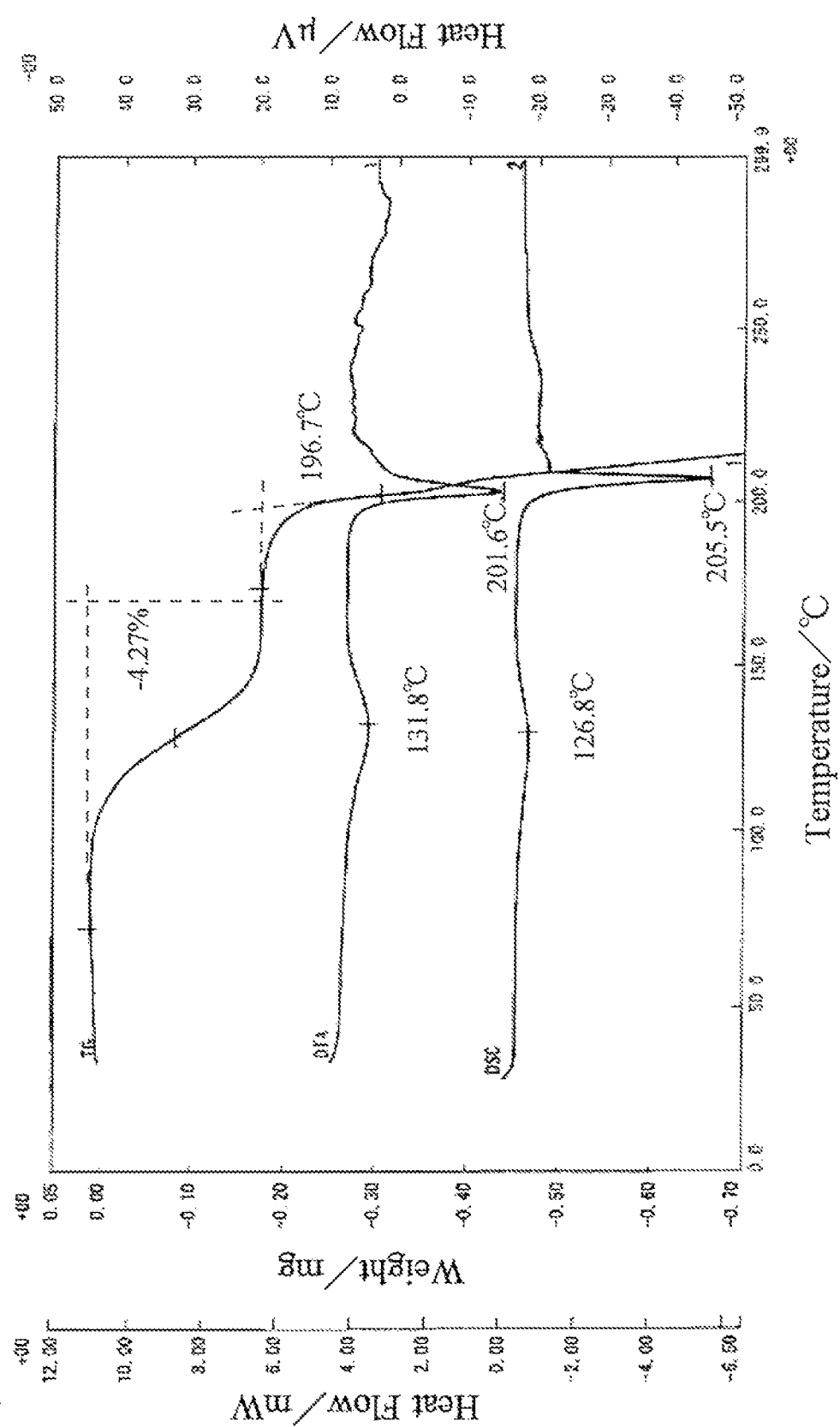
FIG. 6 is a chart illustrating thermal analysis results of D-2-amino-6-phosphonohexanoic acid L-HPGM salt monohydrate obtained in Example 6.

The crude crystals (1) of D-2-amino-6-phosphonohexanoic acid L-HPGM salt monohydrate (3.26 g) were combined with water (19.6 mL), heated to about 70° C. for dissolution, and further combined with methanol (82 mL) added dropwise at the same temperature. The mixture was slowly cooled, stirred at 15° C. for 2 hours, and the precipitated crystals were collected by filtration, washed, and dried. This gave recrystallized crystals (1) of D-2-amino-6-phosphonohexanoic acid L-HPGM salt monohydrate (2.76 g). The thermal analysis results of the obtained compound are presented in FIG. 6.

Mp (DSC): 126.8, 205.5° C. (dec), $[\alpha]_D^{26}$ +66.4 (c1, $H_2O$), 100% de.

IR ($cm^{-1}$): 3458, 2860, 2643, 1733, 1605, 1579, 1523, 1418, 1253, 997, 893.

$^1$H-NMR (600 MHz, $D_2O$) $\delta_H$: 1.38-1.52 (2H, m), 1.52-1.63 (4H, m), 1.80-1.93 (2H, m), 3.73 (1H, dd, $J_{H-H}$=7.2 and 5.1 Hz), 3.81 (3H, s), 5.20 (1H, s), 6.97 (2H, d, $J_{H-H}$=8.6 Hz), 7.34 (2H, d, $J_{H-H}$=8.6 Hz). $^{31}$P-NMR (121 MHz, $D_2O$) $\delta_P$: 26.8.

Figure 7:
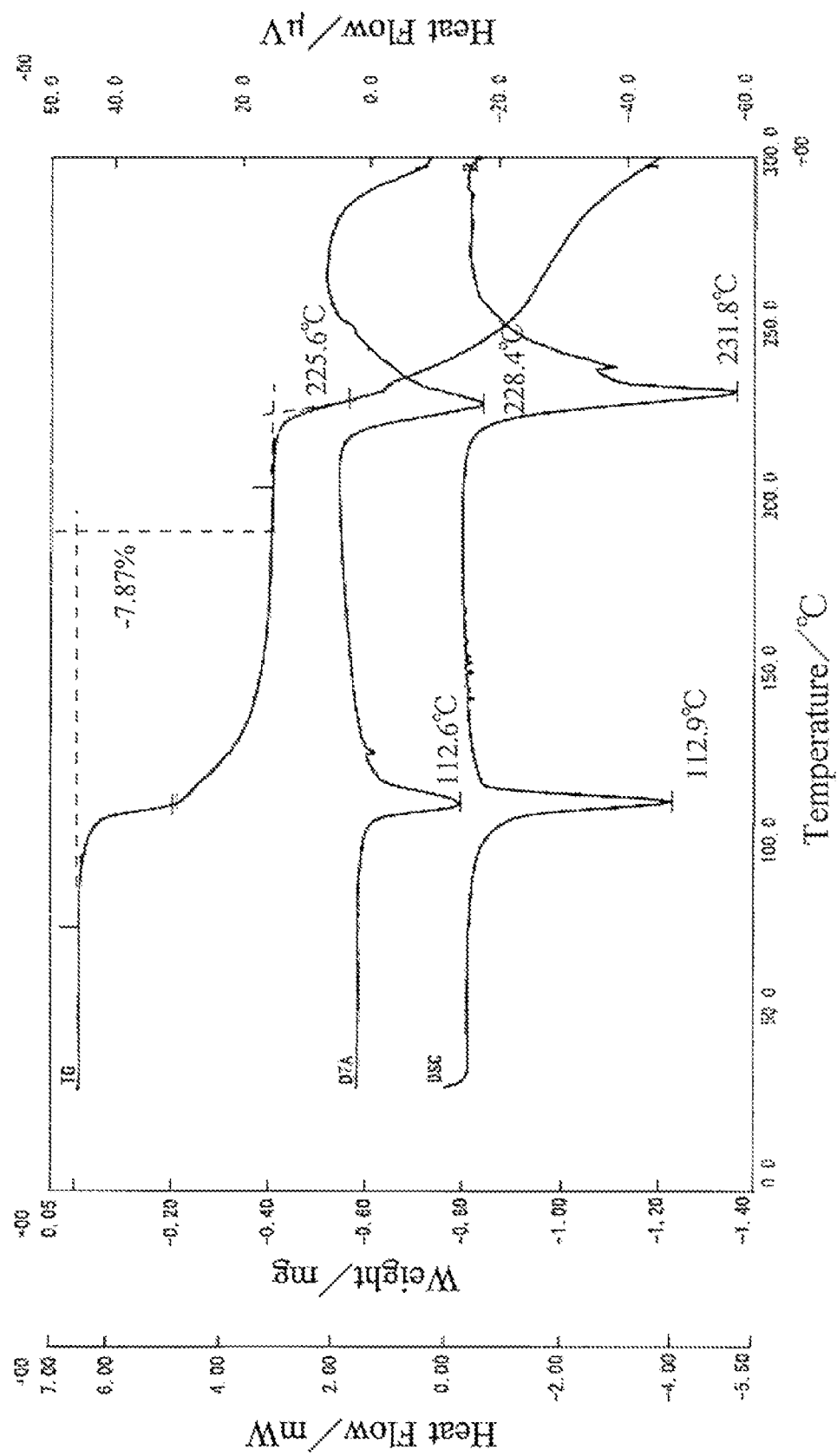
FIG. 7 is a chart illustrating thermal analysis results of D-2-amino-6-phosphonohexanoic acid monohydrate obtained in Example 6.

The recrystallized crystals (1) of D-2-amino-6-phosphonohexanoic acid L-HPGM salt monohydrate (2.66 g) were dissolved in pure water, and the solution was slowly passed through an ion exchange resin AMBERLITE IR-120 (H+) (trade name, supplied by ORGANO CORPORATION) (10.7 mL). After the resin was thoroughly washed with pure water, the passed liquid and the washings were combined and concentrated. The residual solids were combined with and dispersed in methanol (15 mL), collected by filtration, washed with methanol, and dried. This gave colorless crystals of D-2-amino-6-phosphonohexanoic acid monohydrate (1.40 g). The results of thermal analysis of the obtained compound were presented in FIG. 7.

Mp (DSC): 112.9° C., 231.8° C. (dec), $[\alpha]_D^{25}$ −19.6 (c1, 2N—HCl), 100% ee IR ($cm^{-1}$): 3235, 2934, 1705, 1600, 1537, 1148, 1000, 879, 770.

$^1$H-NMR (600 MHz, $D_2O$+DCl) $\delta_H$: 1.43-1.67 (4H, m), 1.74-1.82 (2H, m), 1.85-1.93 (1H, m), 1.93-2.01 (1H, m), 4.06 (1H, dd, $J_{H-H}$=6.4 and 6.4 Hz). $^{31}$P-NMR (121 MHz, $D_2O$) $\delta_P$: 32.6.

Example 7: Optical Resolution of DL-2-Amino-8-Phosphonooctanoic Acid

DL-2-Amino-8-phosphonooctanoic acid monohydrate (50 mg), which was prepared in the preparation example, was combined with each of the optically active basic compounds (0.213 mmol) and corresponding solvents given in Table 3, followed by dissolution with heating. The precipitated crystals were collected by filtration, washed, and dried. This gave a series of diastereomeric salts. The diastereomeric salts were analyzed by chiral HPLC to determine their optical purities (de (%)). The results are presented in Table 3.

TABLE 3

| Optically active basic compound | Solvent (mL) | Diastereomeric salt 2-Amino-8-phosphonooctanoic acid to form the salt | Yield (mg) | de (%) |
|---|---|---|---|---|
| D-Glucamine | Water (0.5)/Methanol (3.0)/IPA (0.3) | L form | 29.4 | 28 |
| L-Valinol | Water (0.5)/Methanol (3.0) | L form | 21.7 | 12 |
| L-Leucinol | Water (0.5)/Methanol (3.0)/IPA (0.5) | D form | 14.7 | 50 |
| (R)-1-Phenylethylamine | Water (0.7)/Methanol (1.7) | L form | 5.1 | 75 |
| D-HPGH | Water (3.4)/Methanol (0.2) | L form | 16.1 | 95 |
| (R)-2-Amino-1-butanol | Water (0.2)/IPA (0.5) | D form | 8 | 82 |

D-HPGH: D-p-Hydroxyphenylglycine hydrazide
Chiral HPLC analysis conditions
Column: SUMICHIRAL OA-5000 (4.6 in diameter by 150 mm)
Mobile phase: 2 mM-CuSO$_4$/H$_2$O:IPA = 92:8, Flow rate: 1.0 ml/min
Detector: UV-254 nm, Temp. 40° C., Sample: 5 mg/10 ml buffer, 10 µl

Example 8: Optical Resolution of DL-2-Amino-8-Phosphonooctanoic Acid Using D-HPGH DL-2-Amino-8-phosphonooctanoic acid monohydrate (5.00 g) was combined with D-HPGH (3.86 g) and water (60 mL), heated and stirred at 80° C., further combined with methanol (30 mL) added gradually, and the mixture was slowly cooled, and stirred at 25° C. for 2 hours. The precipitated crystals were collected by filtration (the filtration mother liquor was used later as "filtration mother liquid*"), washed, and dried. This gave colorless crude crystals of L-2-amino-8-phosphonooctanoic acid D-HPGH salt monohydrate (3.30 g).

$[\alpha]_D^{25}$ −54.5 (c1, N—HCl), 90.6% de. (under the chiral HPLC analysis conditions given with Table 3)

The crude crystals of L-2-amino-8-phosphonooctanoic acid D-HPGH salt monohydrate (3.20 g) were combined with water (112 mL), heated to 85° C. with stirring, and further combined with methanol (112 mL) added dropwise at the same temperature. The mixture was slowly cooled, stirred at 15° C. for 2 hours, and the precipitated crystals were collected by filtration, washed, and dried. This gave recrystallized crystals (1) of L-2-amino-8-phosphonooctanoic acid D-HPGH salt monohydrate (2.80 g).

$[\alpha]_D^{26}$ −52.8 (c1, N—HCl), 99.1% de

Figure 8:
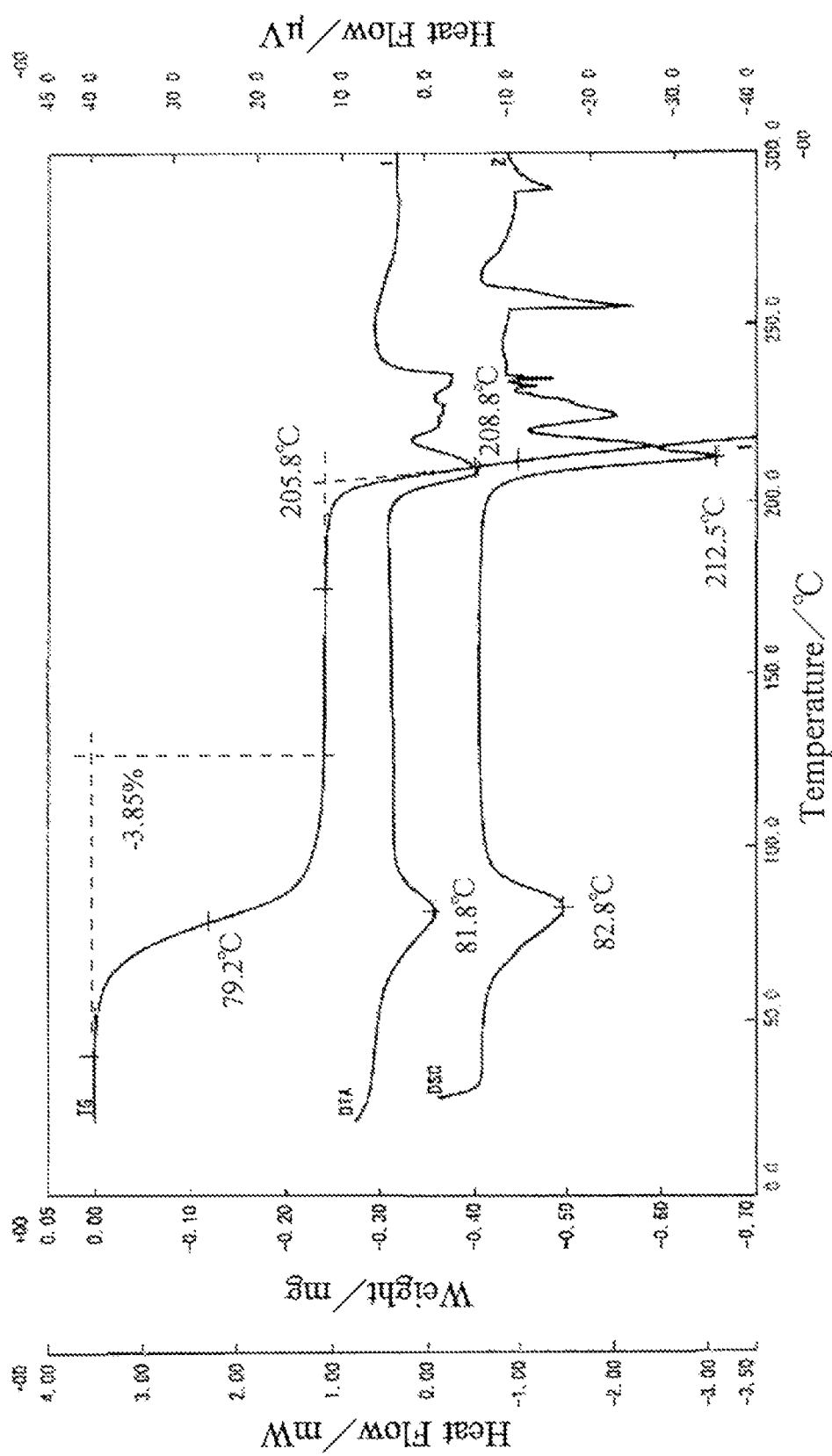
FIG. 8 is a chart illustrating thermal analysis results of L-2-amino-8-phosphonooctanoic acid D-p-hydroxyphenylglycine hydrazide (D-HPGH) salt monohydrate obtained in Example 8.

The recrystallized crystals (1) of L-2-amino-8-phosphonooctanoic acid D-HPGH salt monohydrate (2.70 g) were combined with water (54 mL) and methanol (10 mL), heated to about 75° C. with stirring, and further combined with N—HCl (6.42 mL) to give a solution. The solution was combined with sodium hydrogencarbonate (0.539 g) added in such a manner as to avoid or reduce foaming. The mixture was further combined with methanol (58 mL) added dropwise at the same temperature, slowly cooled, stirred at 15° C. for 2 hours, and the precipitated crystals were collected by filtration, washed, and dried. This gave recrystallized crystals (2) of L-2-amino-8-phosphonooctanoic acid D-HPGH salt monohydrate (2.60 g). The thermal analysis results of the obtained compound are presented in FIG. 8.

Mp (DSC): 82.8° C., 212.5° C. (dec), $[\alpha]_D^{26}$ −51.7 (c1, N—HCl), 100% de.

IR (cm$^{-1}$): 3461, 3334, 3289, 2858, 1682, 1580, 1519, 1263, 999, 911.

$^1$H-NMR (600 MHz, D$_2$O) δ$_H$: 1.33-1.46 (6H, m), 1.48-1.62 (4H, m), 1.80-1.94 (2H, m), 3.74-3.75 (1H, dd, J$_{H-H}$=6.2 and 6.2 Hz). 5.03 (1H, S), 6.97-6.99 (1H, dd, J$_{H-H}$=6.2 and 6.2 Hz), 7.35-7.38 (1H, dd, J$_{H-H}$=6.2 and 6.2 Hz). $^{31}$P-NMR (121 MHz, D$_2$O) δ$_P$: 27.6.

The recrystallized crystals (2) of L-2-amino-8-phosphonooctanoic acid D-HPGH salt monohydrate (2.30 g) were dissolved in pure water, and the solution was slowly passed through an ion exchange resin AMBERLITE IR-120 (H+) (trade name, supplied by ORGANO CORPORATION) (26 mL). After the resin was thoroughly washed with pure water, the passed liquid and the washings were combined and concentrated, and the precipitated crystals were collected by filtration, washed, and dried. This gave colorless crystals of L-2-amino-8-phosphonooctanoic acid monohydrate (1.35 g, yield: 96.0%).

Mp (DSC): 73.0° C., 239.3° C. (dec), $[\alpha]_D^{25}$ +14.9 (c1, 2N HCl), 100% ee (under the chiral HPLC analysis conditions given with Table 3)

IR (cm$^{-1}$): 3144, 2933, 1715, 1634, 1525, 1156, 1030, 887

$^1$H-NMR (300 MHz, D$_2$O) δ$_H$: 1.58-1.86 (2H, m), 2.02-2.25 (2H, m), 4.00-4.06 (1H, t). $^{31}$P-NMR (121 MHz, D$_2$O) δ$_P$: 33.6.

The filtration mother liquor* obtained above was concentrated, the residue was combined with and dissolved in pure water, and the solution was slowly passed through an ion exchange resin AMBERLITE IR-120 (H+) (trade name, supplied by ORGANO CORPORATION) (25 mL). After the resin was thoroughly washed with pure water, the passed liquid and the washings were combined and concentrated, and the residue was dried. This gave colorless crude crystals of D-2-amino-8-phosphonooctanoic acid monohydrate (2.65 g).

$[\alpha]_D^{25}$ −9.0 (c1, N—HCl), 67.7% ee

The crude crystals of D-2-amino-8-phosphonooctanoic acid monohydrate (2.56 g) were combined with L-HPGH (1.98 g) and water (90 mL), heated to 85° C. with stirring, and further combined with methanol (90 mL) added dropwise at the same temperature. The mixture was slowly cooled, stirred at 15° C. for 2 hours, and the precipitated crystals were collected by filtration, washed, and dried. This gave colorless, recrystallized crystals (1) of D-2-amino-8-phosphonooctanoic acid L-HPGH salt monohydrate (3.50 g).

$[\alpha]_D^{25}$ +53.5 (c1, N—HCl), 96.2% de.

The recrystallized crystals (1) of D-2-amino-8-phosphonooctanoic acid L-HPGH salt monohydrate (3.45 g) were combined with water (69 mL) and methanol (10 mL), heated to about 75° C. with stirring, and further combined with N—HCl (8.20 mL) to give a solution. The solution was combined with sodium hydrogencarbonate (0.69 g) added in such a manner as to avoid or reduce foaming, and further combined with methanol (76 mL) added dropwise at the same temperature. The mixture was slowly cooled, stirred at 15° C. for 2 hour, and the precipitated crystals were collected by filtration, washed, and dried. This gave recrystallized crystals (2) of D-2-amino-8-phosphonooctanoic acid L-HPGH salt monohydrate (3.19 g).

Mp (DSC): 81.8° C., 215.1° C., $[\alpha]_D^{25}$ +52.7 (c1, N—HCl), 99.3% ee.

IR (cm$^{-1}$): 3459, 3333, 3288, 2858, 1681, 1579, 1519, 1263, 999, 911.

$^1$H-NMR (600 MHz, D$_2$O) $\delta_H$: 1.33-1.46 (6H, m), 1.48-1.62 (4H, m), 1.80-1.94 (2H, m), 3.73-3.76 (1H, dd, $J_{H-H}$=6.2 and 6.2 Hz), 5.03 (1H, S), 6.97-6.99 (1H, dd, $J_{H-H}$=6.2 and 6.2 Hz), 7.35-7.38 (1H, dd, $J_{H-H}$=6.2 and 6.2 Hz). $^{31}$P-NMR (121 MHz, D$_2$O) $\delta_P$: 27.6.

Figure 9:
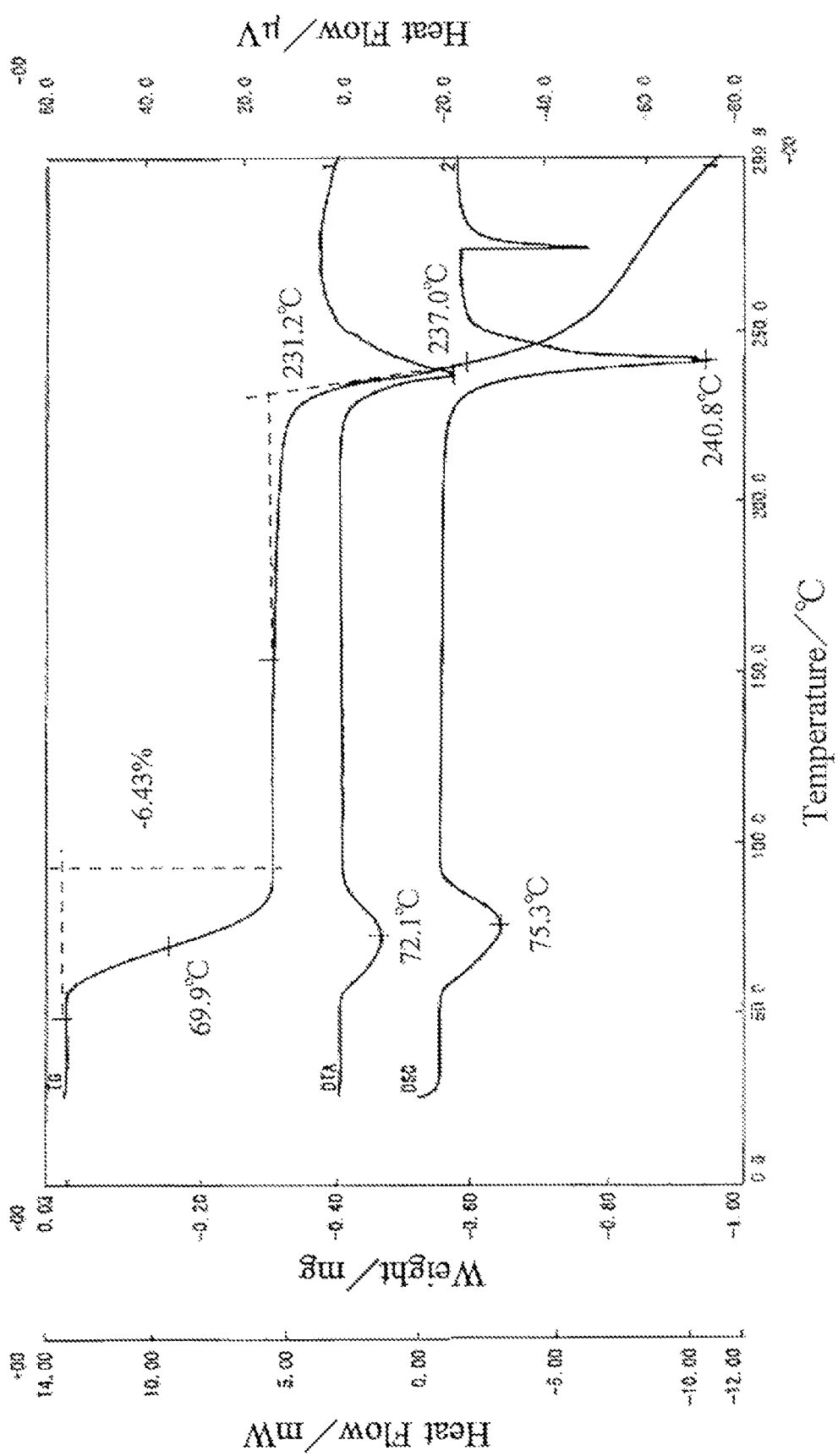
FIG. 9 is a chart illustrating thermal analysis results of D-2-amino-8-phosphonooctanoic acid monohydrate obtained in Example 8.

The recrystallized crystals (2) of D-2-amino-8-phosphonooctanoic acid L-HPGH salt monohydrate (2.30 g) were dissolved in pure water, and the solution was slowly passed through an ion exchange resin AMBERLITE IR-120 (H+) (trade name, supplied by ORGANO CORPORATION) (26 mL). After the resin was thoroughly washed with pure water, the passed liquid and the washings were combined and concentrated, and the precipitated crystals were collected by filtration, washed, and dried. This gave colorless crystals of D-2-amino-8-phosphonooctanoic acid monohydrate (1.37 g). The thermal analysis results of the obtained compound are presented in FIG. 9.

Mp (DSC): 75.3° C., 240.8° C. (dec), $[\alpha]_D^{25}$ −14.8 (c1, 2N HCl), 100% ee IR (cm$^{-1}$): 3142, 2933, 1714, 1633, 1524, 1155, 1030, 887.

$^1$H-NMR (300 MHz, D$_2$O) $\delta_H$: 1.58-1.86 (2H, m), 2.02-2.25 (2H, m), 4.00-4.06 (1H, t). $^{31}$P-NMR (121 MHz, D$_2$O) $\delta_P$: 33.6.

Evaluation for Glutathione Production Promoting Activity

D-2-Amino-8-phosphonooctanoic acid monohydrate obtained in Example 8, which was used as a sample, was evaluated for glutathione production promoting activity by the following method (n=4).

Specifically, normal human epidermal cells were seeded in a 96-well microplate at a density of 2.0×10$^4$ cells per 96 wells, using a normal human epidermal keratinocyte growth medium HuMedia KG2 (trade name, supplied by Kurabo Industries Ltd.).

After 24 hours from the seeding, the medium was exchanged with a normal human epidermal keratinocyte growth medium HuMedia KB2 (trade name, supplied by Kurabo Industries Ltd.) containing the sample in a predetermined concentration, and the cultivation was continued. As a blank, the cells were cultured by a procedure similar to above, except for not using the sample.

After 24-hour cultivation, the cells were disrupted by ultrasonication using a phosphate buffer containing 100 μM phenylmethylsulfonyl fluoride, and the total glutathione amount was determined by glutathione reductase recycling assay.

Specifically, a suspension of the disrupted cells were mixed with reduced nicotinamide adenine dinucleotide phosphate and glutathione reductase, followed by reaction at 37° C. for 10 minutes.

Next, 0.1 M phosphate buffer (containing 0.5 M EDTA, pH 7.5) containing dissolved 10 mM 5,5'-dithiobis(2-nitrobenzoic acid) was added, and the mixture was incubated for 30 minutes. The absorbance at 450 nm was measured immediately after addition, and after incubation for 30 minutes. The difference in absorbance, which is calculated by subtracting the absorbance immediately after addition from the absorbance after 30-minute incubation, was defined as an index for glutathione synthesis quantity.

The total glutathione amount in the disrupted cell suspension was determined on the basis of a calibration curve plotted using oxidized glutathione. The protein content in the disrupted cell suspension was determined using the Pierce Microplate BCA Protein Assay Kit (Thermo SCIENTIFIC). The glutathione synthesis quantity was evaluated for differences from the untreated specimen (blank) and from the positive object by a significant difference test using Student's t-test. The results of the tests, each of which was performed two times, are given in Tables 4-1 (first test) and 4-2 (second test).

TABLE 4

|  | Conc. (μmol/L) | GSH (pmol/μg-protein) | | Protein (μg/well) | |
| --- | --- | --- | --- | --- | --- |
|  |  | Mean ± S.D. | p1 | Mean ± S.D. | p1 |
| Blank (untreated) | 0.00 | 59.3 ± 4.1 | 1.000 | 13.8 ± 0.5 | 1.000 |
| D-2-Amino-8- | 2.00 | 59.5 ± 2.0 | 0.936 | 14.8 ± 0.6 | 0.032 |
| phosphonooctanoic | 10.00 | 60.6 ± 2.3 | 0.610 | 14.9 ± 0.1 | 0.003 |
| acid | 50.00 | 59.7 ± 8.5 | 0.934 | 14.1 ± 0.7 | 0.454 |
| monohydrate | 250.00 | 61.0 ± 3.0 | 0.534 | 14.7 ± 0.3 | 0.017 |
| Blank (untreated) | 0.00 | 31.0 ± 0.7 | 1.000 | 16.7 ± 0.7 | 1.000 |
| D-2-Amino-8- | 2.00 | 35.3 ± 1.7 | 0.003 | 16.1 ± 0.7 | 0.259 |
| phosphonooctanoic | 10.00 | 34.8 ± 1.9 | 0.009 | 15.8 ± 0.5 | 0.076 |
| acid | 50.00 | 34.8 ± 2.6 | 0.029 | 16.3 ± 1.1 | 0.543 |
| monohydrate | 250.00 | 33.6 ± 2.3 | 0.071 | 16.5 ± 0.9 | 0.655 | p1: Significant difference from blank

Tables 4-1 and 4-2 indicate that D-2-amino-8-phosphonooctanoic acid monohydrate obtained in the example has significant glutathione production promoting activity as compared with the blank (untreated specimen).

Tests were performed (n=4) to determine glutathione production promoting activity by a procedure similar to above, except for using, as a sample instead of D-2-amino-8-phosphonooctanoic acid monohydrate, D-2-amino-4-phosphonobutanoic acid L-Arg salt obtained in Example 2, or D-2-amino-4-phosphonobutanoic acid D-Arg salt monohydrate obtained in Example 3.

A test as a referential example was also performed by a procedure similar to above, except for using Nahlsgen (generic name: DL-2-amino-4-[(RSp)-(3-carboxymethylphenoxy)(methoxy)phosphoryl]butanoic acid), instead of the sample.

The results of the tests, each of which was performed two times, are presented in Tables 5-1 (first test) and 5-2 (second test).

TABLE 5

|  | Conc. (µmol/L) | GSH (pmol/µg-protein) | | | Protein (µg/well) | |
|---|---|---|---|---|---|---|
|  |  | Mean ± S.D. | p1 | p2 | Mean ± S.D. | p1 |
| Blank (untreated) | 0.00 | 41.0 ± 3.2 | 1.000 | — | 11.8 ± 0.7 | 1.000 |
| Nahlsgen | 10.00 | 44.7 ± 2.7 | 0.129 | 1.000 | 13.9 ± 0.4 | 0.002 |
| D-2-Amino-4- | 2.00 | 49.2 ± 7.5 | 0.092 |  | 13.5 ± 0.3 | 0.004 |
| phosphonobutanoic | 10.00 | 51.0 ± 1.6 | 0.001 | 0.007 | 13.8 ± 0.6 | 0.005 |
| acid | 50.00 | 43.9 ± 9.3 | 0.589 |  | 13.4 ± 0.6 | 0.010 |
| L-Arg salt | 250.00 | 42.9 ± 9.8 | 0.734 |  | 13.5 ± 0.6 | 0.008 |
| D-2-Amino-4- | 2.00 | 38.6 ± 3.1 | 0.309 |  | 13.7 ± 0.4 | 0.002 |
| phosphonobutanoic | 10.00 | 46.2 ± 1.8 | 0.030 | 0.387 | 13.7 ± 0.5 | 0.004 |
| acid D-Arg | 50.00 | 36.3 ± 4.0 | 0.115 |  | 12.9 ± 0.5 | 0.031 |
| salt monohydrate | 250.00 | 40.9 ± 8.1 | 0.979 |  | 13.6 ± 0.6 | 0.007 |
| Blank (untreated) | 0.00 | 32.4 ± 0.9 | 1.000 | — | 15.3 ± 0.7 | 1.000 |
| Nahlsgen | 10.00 | 36.2 ± 3.4 | 0.078 | 1.000 | 14.4 ± 1.1 | 0.235 |
|  | 50.00 | 36.5 ± 3.9 | 0.085 | 1.000 | 14.6 ± 1.2 | 0.367 |
| D-2-Amino-4- | 2.00 | 37.6 ± 2.2 | 0.005 |  | 16.5 ± 1.4 | 0.182 |
| phosphonobutanoic | 10.00 | 35.4 ± 2.1 | 0.038 | 0.705 | 17.8 ± 1.4 | 0.020 |
| acid | 50.00 | 37.2 ± 3.0 | 0.022 | 0.805 | 18.5 ± 0.7 | 0.001 |
| L-Arg salt | 250.00 | 36.3 ± 1.5 | 0.005 |  | 18.5 ± 0.6 | 0.000 |
| D-2-Amino-4- | 2.00 | 35.8 ± 1.1 | 0.003 |  | 17.7 ± 1.1 | 0.012 |
| phosphonobutanoic | 10.00 | 35.8 ± 1.2 | 0.004 | 0.843 | 17.6 ± 0.7 | 0.003 |
| acid D-Arg | 50.00 | 37.3 ± 1.9 | 0.003 | 0.732 | 17.3 ± 0.7 | 0.006 |
| salt monohydrate | 250.00 | 37.1 ± 1.7 | 0.003 |  | 17.8 ± 0.2 | 0.001 | p1: Significant difference from blank
p2: Significant difference from Nahlsgen at the same concentration Tables 5-1 and 5-2 indicate that D-2-amino-4-phosphonobutanoic acid L-Arg salt and D-2-amino-4-phosphonobutanoic acid D-Arg salt monohydrate, which were obtained in the examples, have significant glutathione production promoting activities comparable to or higher than those of Nahlsgen.

As a summary of the above description, the configurations according to embodiments of the present invention, as well as variations thereof, will be listed below as appendices.

(1) A method for producing an optically active 2-amino-phosphonoalkanoic acid salt, the method including reacting a starting material DL-2-amino-phosphonoalkanoic acid represented by Formula (1) or a hydrate thereof with an optically active basic compound other than an optically active lysine, to give a diastereomeric salt mixture including a first salt (including a hydrate salt) between a D-2-amino-phosphonoalkanoic acid represented by Formula (1-1) and the optically active basic compound and a second salt (including a hydrate salt) between an L-2-amino-phosphonoalkanoic acid represented by Formula (1-2) and the optically active basic compound, and subjecting the diastereomeric salt mixture to fractional crystallization to isolate one of the first and second diastereomeric salts.

(2) The method according to (1), wherein the optically active basic compound is a compound selected from the group consisting of cinchonine, cinchonidine, quinine, quinidine, an optically active arginine, an optically active phenylalaninamide, an optically active ornithine, an optically active tyrosine hydrazide, an optically active 1-phenylpropylamine, an optically active 2-phenylpropylamine, an optically active valinol, an optically active p-hydroxyphenylglycine hydrazide, an optically active p-hydroxyphenylglycine methyl ester, an optically active p-hydroxyphenylglycine ethyl ester, an optically active glucamine, an optically active leucinol, an optically active 1-phenylethylamine, and an optically active 2-amino-1-butanol.

(3) The method according to one of (1) and (2), wherein the starting material is the DL-2-amino-phosphonoalkanoic acid represented by Formula (1) in which m is 1, 3, or 5, or a hydrate of this compound.

(4) The method according to any one of (1) to (3), wherein the hydrate of the DL-2-amino-phosphonoalkanoic acid represented by Formula (1) is used as the starting material, to give, as one of the two diastereomeric salts, the first salt between the D-2-amino-phosphonoalkanoic acid represented by Formula (1-1) and the optically active basic compound, or a hydrate of the first salt, or the second salt between the L-2-amino-phosphonoalkanoic acid represented by Formula (1-2) and the optically active basic compound, or a hydrate of the second salt.

(5) A D-2-amino-phosphonoalkanoic acid salt or a hydrate of the salt, represented by Formula (1-1'-B).

(6) An L-2-amino-phosphonoalkanoic acid salt or a hydrate of the salt, represented by Formula (1-2'-B).

(7) A method for producing an optically active 2-amino-phosphonoalkanoic acid or a hydrate thereof, the method including preparing an optically active 2-amino-phosphonoalkanoic acid salt (including a hydrate salt) by the method according to any one of (1) to (4), and decomposing the prepared compound to give a corresponding optically active 2-amino-phosphonoalkanoic acid or a hydrate thereof which has the same configuration as the compound before decomposition.

(8) A D-2-amino-phosphonoalkanoic acid hydrate represented by Formula (1-1').

(9) An L-2-amino-phosphonoalkanoic acid hydrate represented by Formula (1-2').

(10) A collagen production promoter containing at least one active ingredient selected from the group consisting of D-2-amino-phosphonoalkanoic acid salts or hydrates of the salts each represented by Formula (1-1'-B), L-2-amino-phosphonoalkanoic acid salts or hydrates of the salts each represented by Formula (1-2'-B), D-2-amino-phosphonoalkanoic acid hydrates each represented by Formula (1-1'), and L-2-amino-phosphonoalkanoic acid hydrates each represented by Formula (1-2').

(11) An elastin production promoter containing at least one active ingredient selected from the group consisting of D-2-amino-phosphonoalkanoic acid salts or hydrates of the salts each represented by Formula (1-1'-B), L-2-amino-phosphonoalkanoic acid salts or hydrates of the salts each represented by Formula (1-2'-B), D-2-amino-phosphonoalkanoic acid hydrates each represented by Formula (1-1'), and L-2-amino-phosphonoalkanoic acid hydrates each represented by Formula (1-2').

(12) An HSP47 production promoter containing at least one active ingredient selected from the group consisting of D-2-amino-phosphonoalkanoic acid salts or hydrates of the salts each represented by Formula (1-1'-B), L-2-amino-phosphonoalkanoic acid salts or hydrates of the salts each represented by Formula (1-2'-B), D-2-amino-phosphonoalkanoic acid hydrates each represented by Formula (1-1'), and L-2-amino-phosphonoalkanoic acid hydrates each represented by Formula (1-2').

(13) A glutathione production promoter containing at least one active ingredient selected from the group consisting of D-2-amino-phosphonoalkanoic acid salts or hydrates of the salts each represented by Formula (1-1'-B), L-2-amino-phosphonoalkanoic acid salts or hydrates of the salts each represented by Formula (1-2'-B), D-2-amino-phosphonoalkanoic acid hydrates each represented by Formula (1-1'), and L-2-amino-phosphonoalkanoic acid hydrates each represented by Formula (1-2').

(14) A fillagrin production promoter containing at least one active ingredient selected from the group consisting of D-2-amino-phosphonoalkanoic acid salts or hydrates of the salts each represented by Formula (1-1'-B), L-2-amino-phosphonoalkanoic acid salts or hydrates of the salts each represented by Formula (1-2'-B), D-2-amino-phosphonoalkanoic acid hydrates each represented by Formula (1-1'), and L-2-amino-phosphonoalkanoic acid hydrates each represented by Formula (1-2').

(15) A fillagrin gene expression enhancer containing at least one active ingredient selected from the group consisting of D-2-amino-phosphonoalkanoic acid salts or hydrates of the salts each represented by Formula (1-1'-B), L-2-amino-phosphonoalkanoic acid salts or hydrates of the salts each represented by Formula (1-2'-B), D-2-amino-phosphonoalkanoic acid hydrates each represented by Formula (1-1'), and L-2-amino-phosphonoalkanoic acid hydrates each represented by Formula (1-2').

(16) An epidermic keratinocyte migration-growth stimulator containing at least one active ingredient selected from the group consisting of D-2-amino-phosphonoalkanoic acid salts or hydrates of the salts each represented by Formula (1-1'-B), L-2-amino-phosphonoalkanoic acid salts or hydrates of the salts each represented by Formula (1-2'-B), D-2-amino-phosphonoalkanoic acid hydrates each represented by Formula (1-1'), and L-2-amino-phosphonoalkanoic acid hydrates each represented by Formula (1-2').

(17) A cosmetic for skin care use, containing at least one active ingredient selected from the group consisting of D-2-amino-phosphonoalkanoic acid salts or hydrates of the salts each represented by Formula (1-1'-B), L-2-amino-phosphonoalkanoic acid salts or hydrates of the salts each represented by Formula (1-2'-B), D-2-amino-phosphonoalkanoic acid hydrates each represented by Formula (1-1'), and L-2-amino-phosphonoalkanoic acid hydrates each represented by Formula (1-2').

INDUSTRIAL APPLICABILITY

The present invention uses a starting material DL-2-amino-phosphonoalkanoic acid represented by Formula (1) or a hydrate thereof, which can be produced easily and inexpensively, and enables easy and high-purity production of an optically active D-2-amino-phosphonoalkanoic acid or a hydrate thereof, or an optically active L-2-amino-phosphonoalkanoic acid or a hydrate thereof.

The optically active D-2-amino-phosphonoalkanoic acid or a hydrate thereof, and the L-2-amino-phosphonoalkanoic acid or a hydrate thereof have excellent crystallinity. These compounds absorb approximately no moisture at room temperature and are non-deliquescent. The compounds are storable excellently stably and are easy to handle. The compounds also have a collagen production promoting activity, glutathione production promoting activity, and wound healing promoting activity, have approximately no cytotoxicity, are highly safe, and are advantageously usable typically for the treatment and/or prophylaxis of diseases such as allergic skin diseases, ichthyosis vulgaris, senile xerosis, periodontal diseases, and conjunctivitis.

The invention claimed is:
1. A D-2-amino-phosphonoalkanoic acid salt or a hydrate of the salt, represented by Formula (1-1'-B):

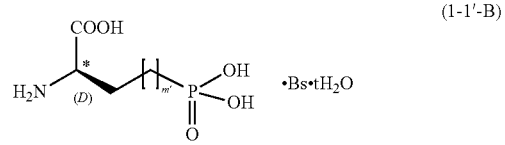

wherein m' represents 1, 3, or 5; t represents a number of 0 to 5; Bs represents an optically active basic compound; and the asterisk marks an asymmetric atom, wherein when m' is 1 in Formula (1-1'-B), the optically active basic compound is selected from the group consisting of a cinchonine, a quinidine, a cinchonidine, an optically active arginine, an optically active p-hydroxyphenylglycine hydrazide, an optically active phenylalaninamide, and an optically active ornithine, when m' is 3 in Formula (1-1'-B), the optically active basic compound is selected from the group consisting of an optically active tyrosine hydrazide, an optically active 1-phenylpropylamine, an optically active valinol, an optically active p-hydroxyphenylglycine methyl ester, an optically active phenylalaninamide, an optically active p-hydroxyphenylglycine hydrazide, and an optically active p-hydroxyphenylglycine ethyl ester, and when m' is 5 in Formula (1-1'-B), the optically active basic compound is selected from the group consisting of an optically active glucamine, an optically active valinol, an optically active leucinol, an optically active 1-phenylethylamine, an optically active p-hydroxyphenylglycine hydrazide, and an optically active 2-amino-1-butanol.

2. An L-2-amino-phosphonoalkanoic acid salt or a hydrate of the salt, represented by Formula (1-2'-B):

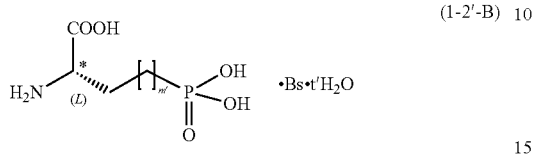

(1-2'-B)

wherein m' represents 1, 3, or 5; t' represents a number of 0 to 5; Bs represents an optically active basic compound; and the asterisk marks an asymmetric atom, wherein when m' is 1 in Formula(1-2'-B), the optically active basic compound is selected from the group consisting of a cinchonine, a quinidine, a cinchonidine, an optically active arginine, an optically active p-hydroxyphenylglycine hydrazide, an optically active phenylalaninamide, and an optically active ornithine, when m' is 3 in Formula(1-2'-B), the optically active basic compound is selected from the group consisting of an optically active tyrosine hydrazide, an optically active 1-phenylpropylamine, an optically active valinol, an optically active p-hydroxyphenylglycine methyl ester, an optically active phenylalaninamide, an optically active p-hydroxyphenylglycine hydrazide, and an optically active p-hydroxyphenylglycine ethyl ester, and when m' is 5 in Formula(1-2'-B), the optically active basic compound is selected from the group consisting of an optically active glucamine, an optically active valinol, an optically active leucinol, an optically active 1-phenylethylamine, an optically active p-hydroxyphenylglycine hydrazide, and an optically active 2-amino-1-butanol.

* * * * *